(12) United States Patent
Moe et al.

(10) Patent No.: US 7,858,121 B2
(45) Date of Patent: *Dec. 28, 2010

(54) EFFERVESCENT ORAL FENTANYL DOSAGE FORM AND METHODS OF ADMINISTERING FENTANYL

(75) Inventors: Derek Moe, Maple Grove, MN (US); Vikas Agarwal, Plymouth, MN (US); Walid Habib, Maple Grove, MN (US)

(73) Assignee: Cima Labs, Inc., Eden Prairie, MN (US)

( * ) Notice: Subject to any disclaimer, the term of this patent is extended or adjusted under 35 U.S.C. 154(b) by 1263 days.

This patent is subject to a terminal disclaimer.

(21) Appl. No.: 11/027,353

(22) Filed: Dec. 30, 2004

(65) Prior Publication Data

US 2005/0142198 A1    Jun. 30, 2005

Related U.S. Application Data

(60) Provisional application No. 60/533,619, filed on Dec. 31, 2003, provisional application No. 60/615,785, filed on Oct. 4, 2004.

(51) Int. Cl.
*A61K 9/20* (2006.01)
*A61K 9/46* (2006.01)

(52) U.S. Cl. .................. 424/464; 424/465; 424/466

(58) Field of Classification Search ............... None
See application file for complete search history.

(56) References Cited

U.S. PATENT DOCUMENTS

| | | | |
|---|---|---|---|
| 1,262,888 A | 4/1918 | Westlake | |
| 1,263,888 A | 4/1918 | Westlake | |
| 3,131,123 A | 4/1964 | Masquelier | |
| 3,577,490 A | 5/1971 | Welsh et al. | |
| 3,888,976 A | 6/1975 | Mlkvy et al. | |
| 3,961,041 A | 6/1976 | Nishimura et al. | |
| 3,962,417 A | 6/1976 | Howell | |
| 3,972,995 A | 8/1976 | Tsuk et al. | |
| 4,147,768 A | 4/1979 | Shaffer et al. | |
| 4,187,286 A | 2/1980 | Marcus | |
| 4,289,751 A | 9/1981 | Windheuser | |
| 4,443,428 A | 4/1984 | Oshlack et al. | |
| 4,493,848 A | 1/1985 | LaHann et al. | |
| 4,503,031 A | 3/1985 | Glassman | |
| 4,599,342 A | 7/1986 | LaHann | |
| 4,613,497 A | 9/1986 | Chaukin | |
| 4,639,368 A | 1/1987 | Niazi et al. | |
| 4,671,953 A | 6/1987 | Stanley et al. | |
| 4,687,662 A | 8/1987 | Schobel | |
| 4,689,218 A | 8/1987 | Gazzaniga et al. | |
| 4,725,427 A | 2/1988 | Ashmead | |
| 4,753,792 A | 6/1988 | Aberg | |
| 4,756,710 A | 7/1988 | Bondi et al. | |
| 4,853,211 A | 8/1989 | Kurobe et al. | |
| 4,863,737 A | 9/1989 | Stanley et al. | |
| 4,940,588 A | 7/1990 | Sparks | |
| 5,002,771 A | 3/1991 | Purkaystha et al. | |
| 5,028,411 A | 7/1991 | Callingham et al. | |
| 5,053,396 A | 10/1991 | Blass | |
| 5,055,306 A | 10/1991 | Barry et al. | |
| 5,073,374 A * | 12/1991 | McCarty | 424/435 |
| 5,102,666 A | 4/1992 | Acharya | |
| 5,135,752 A | 8/1992 | Snipes | |
| 5,178,878 A * | 1/1993 | Wehling et al. | 424/466 |
| 5,223,264 A | 6/1993 | Wehling et al. | |
| 5,314,904 A | 5/1994 | Egidio et al. | |
| 5,387,420 A | 2/1995 | Mitchell et al. | |
| 5,445,827 A | 8/1995 | Fritsch et al. | |
| 5,458,879 A | 10/1995 | Singh et al. | |
| 5,464,632 A | 11/1995 | Cousin et al. | |
| 5,468,504 A | 11/1995 | Schaeffer | |
| 5,501,861 A | 3/1996 | Makino et al. | |
| 5,503,846 A | 4/1996 | Wehling et al. | |
| 5,550,861 A | 8/1996 | Chan et al. | |
| 5,559,096 A | 9/1996 | Edwards et al. | |
| 5,607,697 A | 3/1997 | Alkire et al. | |
| 5,624,687 A | 4/1997 | Yano et al. | |
| 5,626,866 A | 5/1997 | Ebert et al. | |
| 5,646,151 A | 7/1997 | Kruse et al. | |
| 5,656,284 A | 8/1997 | Balkin | |
| 5,720,974 A | 2/1998 | Makino | |
| 5,785,989 A | 7/1998 | Stanley et al. | |
| 5,807,688 A | 9/1998 | Blackburn et al. | |
| 5,853,748 A | 12/1998 | New | |

(Continued)

FOREIGN PATENT DOCUMENTS

CA    2211586    8/1996

(Continued)

OTHER PUBLICATIONS

Stanley et al, "Novel Delivery Systems: Oral Transmucosal and Intranasal Transmucosal", Journal of Pain and Sympton Management, vol. 7, No. 3, Apr. 1992, pp. 163-171.

(Continued)

*Primary Examiner*—Humera N Sheikh

(57) ABSTRACT

Fentanyl-containing dosage forms and methods using same are described. These dosage forms include substantially less fentanyl by weight than known oral formulation and have advantages in terms of reduced cost and reduced side effects. These dosage forms are intended for oral administration of fentanyl across the oral mucosa.

14 Claims, No Drawings

U.S. PATENT DOCUMENTS

| | | | |
|---|---|---|---|
| 5,900,252 | A | 5/1999 | Calanchi et al. |
| 5,952,004 | A | 9/1999 | Rudnic et al. |
| 5,958,455 | A | 9/1999 | Roser et al. |
| 5,958,458 | A | 9/1999 | Norling et al. |
| 6,034,085 | A | 3/2000 | Joshi et al. |
| 6,068,853 | A | 5/2000 | Giannos et al. |
| 6,071,539 | A | 6/2000 | Robinson et al. |
| 6,106,861 | A | 8/2000 | Cheveau |
| 6,117,912 | A | 9/2000 | DiSanto |
| 6,129,906 | A | 10/2000 | Steventon |
| 6,155,423 | A | 12/2000 | Katzner et al. |
| 6,200,604 | B1 | 3/2001 | Pather et al. |
| 6,242,002 | B1 | 6/2001 | Tritthart et al. |
| 6,264,981 | B1 | 7/2001 | Zhang et al. |
| 6,316,027 | B1 | 11/2001 | Clarke et al. |
| 6,326,360 | B1 | 12/2001 | Kanazawa et al. |
| 6,326,384 | B1 | 12/2001 | Whittle et al. |
| 6,350,470 | B1 | 2/2002 | Pather et al. |
| 6,368,625 | B1 | 4/2002 | Siebert et al. |
| 6,391,335 | B1 | 5/2002 | Pather et al. |
| 6,488,961 | B1 | 12/2002 | Robinson et al. |
| 6,509,036 | B2 | 1/2003 | Pather et al. |
| 6,576,250 | B1 | 6/2003 | Pather et al. |
| 6,641,838 | B2 | 11/2003 | Pather et al. |
| 6,680,071 | B1 | 1/2004 | Johnson et al. |
| 6,759,059 | B1 | 7/2004 | Petterson et al. |
| 6,761,910 | B1 | 7/2004 | Petterson et al. |
| 6,764,696 | B2 | 7/2004 | Pather et al. |
| 6,974,590 | B2 | 12/2005 | Pather et al. |
| 2001/0006677 | A1 | 7/2001 | McGinity et al. |
| 2002/0160991 | A1* | 10/2002 | Shao .................... 514/183 |
| 2004/0213855 | A1 | 10/2004 | Petterson et al. |
| 2005/0037072 | A1 | 2/2005 | Pather et al. |
| 2005/0142197 | A1 | 6/2005 | Moe et al. |
| 2005/0163838 | A1 | 7/2005 | Moe |
| 2005/0169989 | A1 | 8/2005 | Moe et al. |
| 2006/0292219 | A1 | 12/2006 | Pather et al. |
| 2007/0036853 | A1 | 2/2007 | Agarwal et al. |

FOREIGN PATENT DOCUMENTS

| | | |
|---|---|---|
| CA | 2254060 | 1/1997 |
| CA | 2218370 | 2/1997 |
| EP | 0 197 504 A1 | 10/1986 |
| EP | 0 354 973 B2 | 2/1990 |
| EP | 0361680 A2 | 4/1990 |
| EP | 1 062 952 A | 12/2000 |
| GB | 3160 | 10/1872 |
| GB | 2307857 A | 6/1997 |
| JP | 7-277959 | 10/1995 |
| TW | 36236 | 4/1981 |
| TW | 40484 | 12/1981 |
| TW | 200611697 | 4/2006 |
| WO | WO-91/04757 | 4/1991 |
| WO | 95/07701 | 3/1995 |
| WO | WO-95/27482 A1 | 10/1995 |
| WO | WO-95/34291 A1 | 12/1995 |
| WO | WO-96/29993 A1 | 10/1996 |
| WO | WO-97/17067 A1 | 5/1997 |
| WO | WO-99/45934 A | 9/1999 |
| WO | WO-99/49842 A1 | 10/1999 |
| WO | WO-00/09093 A | 2/2000 |
| WO | WO-00/35418 A1 | 6/2000 |
| WO | 00/59423 | 10/2000 |
| WO | WO-2004/067004 | 8/2004 |

OTHER PUBLICATIONS

Weinberg et al., "Sublingual absorption of selected opioid analgesics", Clinical Pharmacology and Therapeutics, Sep. 1988, 44 (3), pp. 335-342.

Streisand et al., "Buccal absorption of fentanyl is pH-dependent in dogs", Anesthesiology, (Mar. 1995), 82 (3), pp. 759-764.

Chen et al., "Studies on formulations of fentanyl buccal adhesive tablets", Zhonggup Yiyao Gongye Zazhi, 1997, 28 (3), 129-131.

Supplementary European Search Report, EP 00 92 6341, Dated Nov. 23, 2005.

Audus, K., et al, "The Use of Cultured Epithelial and Endothelial Cells for Drug Transport and Metabolism Studies", Pharmaceutical Research, vol. 7, No. 5, 1990, p. 435.

U.S. Appl. No. 09/661,693, filed Sep. 14, 2000.

Hessel, P.G., et al., "A Comparison of the availability of prochlorperazinc following i.m. buccal and oral administration", International Journal of Pharmaceutics, Jun. 1, 1989, vol. 52, Issue 2, p. 159-164.

Pather et al.,"Buccal Delivery—Enhanced Buccal Delivery of Fentanyl Using the Oravescent Drug Delivery System", Drug Delivery Tech. , vol. 1, No. 1, Oct. 2001.

James W. Conine, Special Tablets, in Pharmaceutical Dosage Forms: Tablets vol. 1, 329 (Herbert A. Lieberman et al. eds, 1989).

Alternative Routes of Drug Administration—Advantages and Disadvantages (Subject Review), American Academy of Pediatrics Committee on Drugs, Pediatrics, vol. 100, No. 1 Jul. 1997, 143, 147.

Ranade, V.V.; Drug Delivery Systems Part 5B. Oral Drug Delivery, The Journal of Clinical Pharmacology, Feb. 1991, pp. 98-115, vol. 31.

Giannos, S.A.; Dinh, S.M.; Berner, B.; Temporally Controlled Drug Delivery Systems: Coupling of pH Oscillators with Membrane Diffusion, Journal of Pharmaceutical Sciences, May 1995, pp. 539-543, vol. 84, No. 5.

Amighi, K.; Timmermans, J.; Puigdevall, J.; Baltes, E.; Moës, A.. J.; Peroral Sustained-Release Film-Coated Pellets as a Means to Overcome Physicochemical and Biological Drug-Related Problems. I. In Vitro Development and Evaluation, Drug Development and Industrial Pharmacy, 1998, pp. 509-515, vol. 24, No. 6.

Sorasuchart, W.; Wardrop, J.; Ayers, J.; Drug Release from Spray Layered and Coated Drug-Containing Beads: Effects of pH and Comparison of Different Dissolution Methods, Drug Development and Industrial Pharmacy, 1999, pp. 1093-1098, vol. 25, No. 10.

Berko, S.; Regdon Jun, G.; Erös, I.; Influence of pH Change on Drug Release from Rectal Suppositories, Die Pharmazie, Apr. 2000, p. 324, vol. 55., Govi-Verlag Pharmazeutischer Verlag GmbH, Eschborn.

Streubel, A.; Siepmann, J.; Dashevsky, A.; Bodmeier, R.; pH-Independent Release of a Weakly Basic Drug from Water-Insoluble and -Soluble Matrix Tablets, Journal of Controlled Release, 2000, pp. 101-110, vol. 67.

*Cephalon Inc., and CIMA Labs, Inc., v. Watson Pharmaceuticals Inc., and Watson Laboratories Inc.*, complaint for patent infringement, Civil Action # 08-330, (2008).

*Cephalon Inc., and CIMA Labs, Inc., v. Barr Pharmaceuticals Inc., and Barr Laboratories Inc.*, complaint for patent infringement, (2008).

*Cephalon Inc., and CIMA Labs, Inc., v. Barr Pharmaceuticals Inc., and Barr Laboratories Inc.*, Case No. 08-cv-00455 (UNA), answer, affirmative defenses and counterclaims, (2008).

Sterne, Kessler, Letter dated Jun. 9, 2008.

Sterne, Kessler, Letter dated Jun. 27, 2008.

*Cephalon v. Watson*, Para. IV—Redacted, (2008).

Office Action for corresponding European Application 04 815 715, (2008).

Weatherell et al., "The Flow of Saliva and its Influence on the Movement, Deposition, and Removal of Drugs Administered to the Oral Cavity" Oral Mucosal Drug Delivery, Ch. 8, pp. 157-187 (1996).

Eichman, J.D., Thesis "Mechanistic Studies on Effervescent-Induced Permeability Enhancement" (catalogued at the University of Wisconsin-Madison on Sep. 18, 1998) (on file with the University of Wisconsin-Madison).

Sasahara et al., "Dosage Form Design for Improvement of Bioavailability of Levodopa II: Bioavailability of Marketed Levodopa Preparations in Dogs and Parkinsonian Patients" J. Pharm. Sci. 69(3):261-65 (1980).

Aungst, B.J., "Oral Mucosal Permeation Enhancement: Possibilities and Limitations" Oral Mucosal Drug Delivery, Ch. 4, pp. 65-81 (1996).

Squier, C.A., and Wertz, P.W., "Structure and Function of the Oral Mucosa and Implications for Drug Delivery" Oral Mucosal Drug Delivery, Ch. 1, pp. 1-19 (1996).

Sasahara et al., "Dosage Form Design for Improvement of Bioavailibity of Levodopa IV: Possible Causes of Low Bioavailability of Oral Levodopa in Dogs" J. Pharm. Sci. 70(7):730-33 (1981).

Soskolone, W.A., and Friedman, M., "Intra-periodontal Pocket Drug Delivery Systems" Oral Mucosal Drug Delivery, Ch. 14, pp. 359-73 (1996).

U.S. Appl. No. 10/936,185, filed Mar. 2, 2010, Pather et al.

Helene Hagerstrom, "Polymer Gels as Pharmaceutical Dosage Forms" Thesis (Comprehensive Summaries of Uppsala Dissertations from the Faculty of Pharmacy 293) 2003.

Susanne Bredenberg, "New Concepts in Administration of Drugs in Tablet Form" Thesis (comprehensive summaries of Uppsala Dissertations from the Faculty of Pharmacy 287) 2003.

Pharmaceutical Dosage Forms—Tablets vol. 1, 2nd ed., Herbert A. Lieberman, ed. pp. 372-376, 1990.

Zhang, H., and Robinson, J.R., "Routes of Drug Transport Across Oral Mucosa" Oral Mucosal Drug Delivery, Ch. 3, pp. 51-61 (1996).

Zhang, H., and Robinson, J.R., "In Vitro Methods for Measuring Permeability of the Oral Mucosal" Oral Mucosal Drug Delivery, Ch. 5, pp. 85-97 (1996).

Rassing, M.R., "Specialized Oral Mucosal Drug Delivery Systems: Chewing Gum" Oral Mucosal Drug Delivery, Ch. 13, pp. 319-353 (1996).

Eichman, J.D., and Robinson, J.R., "Mechanistic Studies on Effervescent-Induced Permeability Enhancement" Pharm. Res. 15(6):925-30 (1998).

Sasahara et al., "Dosage Form Design for Improvement of Bioavailability of Levodopa V: Absorption and Metabolism of Levodopa in Intestinal Segments of Dogs" J. Pharm. Sci. 70(10):1157-60 (1981). ######.

Wertz et al., "Biochemical Basis of the Permeability Barrier in Skin and Oral Mucosa" Oral Mucosal Drug Delivery, Ch. 2, pp. 27-41 (1996).

Sasahara et al., "Dosage Form Design for Improvement of Bioavailability of Levodopa III: Influence of Dose on Pharmacokinetic Behavior of Levodopa in Dogs and Parkinsonian Patients" J. Pharm. Sci. 69(12):1374-78 (1980).###.

Kellaway, I.W., and Warren, S.J., "Mucoadhesive Hydrogels for Buccal Delivery" Oral Mucosal Drug Delivery, Ch. 10, pp. 221-237 (1996).

Rathbone et al., "Systemic Oral Mucosal Drug Delivery and Delivery Systems" Oral Mucosal Drug Delivery, Ch. 11, pp. 241-275 (1996).

Schenkels et al., "Salivary Mucins: Their Role in Oral Mucosal Barrier Function and Drug Delivery" Oral Mucosal Drug Delivery, Ch. 9, pp. 191-211 (1996).

DeGrande et al., "Specialized Oral Mucosal Drug Delivery Systems: Patches" Oral Mucosal Drug Delivery, Ch. 12, pp. 285-313 (1996). #########.

Rathbone et al., "In Vivo Techniques for Studying the Oral Mucosal Absorption Characteristics of Drugs in Animals and Humans" Oral Mucosal Drug Delivery, Ch. 7, pp. 121-151 (1996).

Nishimura et al., "Dosage Form Design for Improvement of Bioavailability of Levodopa VI: Formulation of Effervescent Enteric-Coated Tablets" J. Pharm. Sci. 73(7):942-46 (1984).######.

Audus, K.L., "Buccal Epithelial Cell Cultures as a Model to Study Oral Mucosal Drug Transport and Metabolism" Oral Mucosal Drug Delivery, Ch. 6, pp. 101-115 (1996).

* cited by examiner

EFFERVESCENT ORAL FENTANYL DOSAGE FORM AND METHODS OF ADMINISTERING FENTANYL

CROSS-REFERENCE TO RELATED APPLICATIONS

This application claims the benefit of the filing date of U.S. Provisional Patent Application Nos. 60/533,619, filed Dec. 31, 2003, and 60/615,785, filed Oct. 4, 2004, the disclosures of which are hereby incorporated herein by reference.

BACKGROUND OF THE INVENTION

Fentanyl (CAS Registry No. 437-38-7) N-phenyl-N-[1-(2-phenyl-ethyl)-4-piperidinyl]propanamide and its salts, in particular its citrate salt (CAS Registry No. 990-73-8) are opiates, controlled substances, and extremely potent narcotic analgesics. Fentanyl and its citrate salt are currently marketed by a number of companies in a number of delivery formats. Fentanyl citrate, for example, is available as an injectable and an oral lozenge on a stick, the latter sold under the trade name ACTIQ. Three patents are identified in the FDA publication Approved Drug Products With Therapeutic Equivalence Evaluations (hereinafter "the Orange Book") as relating to ACTIQ: U.S. Pat. Nos. 4,671,953, 4,863,737 and 5,785,989. A second form of ACTIQ may also be available. This form may be a compressed tablet on a stick. Like the original ACTIQ lozenge, this second form is believed to exhibit the same disintegration rate, $T_{max}$, $C_{max}$ and AUC as the original lozenge. Accordingly, they will be discussed collectively, except where expressly stated otherwise or as the context dictates.

A review of the package insert information for ACTIQ sold by Cephalon, Inc., 145 Brandy Wine Parkway West, Chester, Pa. 19380, available in the Physician's Desk Reference, 57th ed. 2003 at page 1184, brings instant perspective on the seriousness of the afflictions of the patients who take it. According to its label, ACTIQ "is indicated only for the management of break-through cancer pain in patients with malignancies who are already receiving and who are tolerant to opiate therapy for their underlying persistent cancer pain." (Id., emphasis in original). The text of the ACTIQ label is hereby incorporated by reference.

In clinical trials of ACTIQ, breakthrough cancer pain was defined as a transient flare of moderate-to-severe pain occurring in cancer patients experiencing persistent cancer pain otherwise controlled with maintenance doses of opiate medications, including at least 60 mg of morphine/day, 50 micrograms transdermal fentanyl/hour or equianalgesic dose of another opiate for a week or longer. Thus patients receiving ACTIQ are patients with suddenly intolerable pain, which flares up despite undergoing chronic analgesic treatment. Providing pain relief from such breakthrough pain is inexorably linked with the patient's immediate quality of life. And for such patients, providing breakthrough pain relief may be the only thing that medical science can offer.

As with many things in medicine, there is always room for improvement. Fentanyl is an expensive drug, costing manufacturers as much as $100/gram or more. While cost is by no means an overriding issue, the cost of medication is an issue to be considered. A formulation that allows for a reduction in the amount of fentanyl could reduce the overall cost of a patient's care.

Far more importantly, a reduction in dose of such a potent opiate while still achieving beneficial management of breakthrough pain in cancer patients, has very far reaching and desirable consequences in terms of patients overall care. Opiate mu-receptor agonists, including fentanyl, produce dose dependent respiratory depression. Serious or fatal respiratory depression can occur, even at recommended doses, in vulnerable individuals. As with other potent opiates, fentanyl has been associated with cases of serious and fatal respiratory depression in opiate non-tolerant individuals. Thus, the initial dose of ACTIQ used to treat episodes of breakthrough cancer patients should be 200 micrograms and each patient should be individually titrated to provide adequate analgesia while minimizing side effects. And the side effects, even those that are not life threatening, can be significant.

In addition, fentanyl, as a mu-opiate agonist can produce drug dependence and tolerance. Drug dependence in and of itself is not necessarily a problem with these types of cancer patients. But, fentanyl can be used in the treatment of other types of pain as well. In such treatment protocols, dependence and tolerance may be significant issues. Moreover, cancer patients are generally undergoing heavy medication. The longer that a lower dose of medication can be provided, the better.

U.S. Pat. No. 6,200,604 ("the '604 patent"), which issued Mar. 13, 2001 to CIMA LABS INC., 10000 Valley View Road, Eden Prairie, Minn. 55344, exemplifies two fentanyl formulations each containing 36% effervescents and 1.57 milligrams of fentanyl citrate. See example I thereof, col. 5, ln. 60 through col. 6, ln. 30. The '604 patent describes the use of, amongst other things, effervescence as a penetration enhancer for influencing oral drug absorption. See also U.S. Pat. Nos. 6,759,059 and 6,680,071. See also Brendenberg, S., 2003 New Concepts in Administration of Drugs in Tablet Form: Formulation and Evaluation of a Sublingual Tablet for Rapid Absorption, and Presentation of an Individualized Dose Administration System, Acta Universitatis Upsaliensis. *Comprehensive Summaries of Uppsala Dissertations from the Faculty of Pharmacy*, 287, 83 pp. Uppsala ISBN 91-554-5600-6.

If lower doses of fentanyl which nonetheless provide similar pain relief could be achieved, patients could obtain comparable benefit with much less drug at lower cost and with a reduced risk of side effects. Thus, improvement in the administration of fentanyl is still desirable.

SUMMARY OF THE INVENTION

The present invention relates to an orally disintegrable dosage form, methods of using such dosage forms to treat pain and uses for the manufacture of a medicament, wherein fentanyl, or one or more of its pharmaceutically acceptable salts (where "fentanyl" is recited, it should be assumed to include all pharmaceutically acceptable salts unless the text or context suggests otherwise) are administered orally at doses containing at least about 45% less fentanyl when compared to noneffervescent lollipop formulations (both lozenge and pressed tablets) currently available. Despite the lower dose, these orally disintegrable dosage forms of the invention should have a $C_{max}$ which is comparable to other dosage forms containing much more, e.g., about twice as much drug. "Comparable" in this context means that the $C_{max}$ of a dosage form of the present invention is at least about 75% to about 125% of that of ACTIQ having about twice as much fentanyl. Thus, if a 400 microgram tablet in accordance with the present invention was compared to a 400 microgram ACTIQ lollipop, and both were compared to an 800 microgram ACTIQ lollipop, the tablet in accordance with the present invention would have a $C_{max}$, which is at least about 75% to about 125% of the $C_{max}$ of the 800 microgram ACTIQ formulation. The 400 microgram ACTIQ formulation will have a much lower $C_{max}$. This is true for doses of up to and including about 1000 micrograms based on the weight of fentanyl in free form. More preferably, "comparable" in the context of the invention may also mean that the $C_{max}$ of a dosage form of the present invention is between about 80 and about 120% that of ACTIQ having about twice as much fentanyl by weight. This can also be referred to as being "highly comparable." Even more preferably, "comparable" in the context of the invention may also mean that the $C_{max}$ of a dosage form of the present invention is between about 85 and about 115% that of ACTIQ having about twice as much fentanyl by weight. This can also be referred to as being "very highly comparable."

"Oral dosage form" in the context of the invention preferably excludes lollipop-like lozenges like ACTIQ® and instead includes orally disintegrable/dissolvable tablets, capsules, caplets, gels, creams, films and the like. Preferably, these dosage forms are effervescent tablets. In addition, they may include a pH adjusting substance. In addition, they may include a disintegrant and also possibly a filler, preferably ones which facilitate or even enhance the ratio of Cmax to dose and/or dose reduction realized in accordance with the invention. Generally, these dosage forms are applied to or placed in a specific place in the oral cavity and they remain there while they disintegrate and/or dissolve, generally in a period of about 10 to 30 minutes. The active ingredient, fentanyl is transported across or traverses the oral mucosa in at least the area in which the dosage form was placed. Often, a much greater percentage of the active is delivered to the bloodstream through the oval mucosa as opposed to the rest of the digestive tract.

In another preferred aspect of the present invention, there is provided an orally disintegrable effervescent dosage form designed for the administration of fentanyl and/or pharmaceutically acceptable salts thereof through the oral cavity such as through buccal, gingival or sublingual administration routes, rather than being swallowed. This formulation preferably will not include a stick or other such device permitting it to be easily held in the hand of a patient or removed from the mouth once the dosage form has been wetted in the mouth. In addition, the dosage form will include at least about 45% less fentanyl (based on its weight calculated as a free base material) and more preferably between about 45% and about 55% less fentanyl when compared to the corresponding ACTIQ® product. Yet they will be comparable, preferably highly comparable and even more preferably very highly comparable in terms of $C_{max}$, as well as generally equally efficacious.

Thus, if 1600 micrograms of fentanyl is provided in an ACTIQ® formulation, the corresponding dosage form in accordance with the present invention would include approximately 880 micrograms of fentanyl or less. More preferably, it would include about 800 micrograms of fentanyl. Yet despite such a dramatic reduction in the amount of drug, at least one or more of the traditional pharmacokinetic properties measured for various drugs would be similar, if not superior. For example, in accordance with the present invention, formulations may have a shorter $T_{max}$, the time at which the maximum concentration is reached and/or a comparable, if not superior, $C_{max}$, the highest observed concentration in the blood of a patient after administration, when compared to the corresponding ACTIQ® product containing at least 80% more fentanyl. AUC or areas under the curve will be generally linear from dose to dose in accordance with one preferred aspect of the present invention. These formulations of the invention also preferably provide a faster onset of pain relief when compared to currently available oral dosage forms.

In another embodiment, the dosage forms of the invention provide a ratio of $C_{max}$ to dose in the dosage range of 100-1000 micrograms of between about 2.0 and about 4.0 picograms/mL/microgram. That is picograms of fentanyl base per mL of serum or a proportionate amount if determined in blood or other fluid normalized per microgram of the dose. More preferably, the ratio is about 2.5 to about 3.5 and even more preferably between about 2.7 and about 3.5 picograms/mL/microgram. These ranges are based on mean data calculated for at least 10 patents in an appropriate clinical trial. In contrast, testing has established that ACTIQ provides a ratio of about 1.4 picograms/mL/microgram. Thus for dosage forms containing the same amount of fentanyl, the present invention can provide about twice the $C_{max}$, if not more. "Between" includes the end points, unless specified otherwise.

Also preferred as one aspect in accordance with the present invention are effervescent dosage forms of fentanyl designed to be administered buccally, gingivally or sublingually containing one milligram or less of fentanyl, by weight, based on the weight of the free base material and having a $T_{max}$ of less than about 1.5 hours and most preferably less than about 1 hour. Yet these dosage forms will have a desirable $C_{max}$ as discussed above of between about 2.0 and about 4.0 picograms/mL/microgram. Methods of administering these dosage forms to treat pain are also contemplated.

In another particularly preferred embodiment in accordance with the present invention, formulations include effervescence to act as a penetration enhancer with or without, but preferably with an additional pH adjusting substance. Most preferably, the pH adjusting substance is something other than one of the components, compounds, or molecules used to generate effervescence.

In one embodiment, the pH adjusting substance is selected and provided in an amount which is capable of producing a change in the localized pH in the microenvironment at the surface contact area of the oral mucosa and the dosage form (or portions of it as it disintegrates/dissolves) once placed in the mouth of a patient ("localized pH") of at least 0.5 pH units, more preferably 1.0 pH units.

Particularly preferred dosage forms also include a disintegrant which permits the dose reduction and/or ratio of $C_{max}$ and dose described herein. One particularly preferred example of a disintegrant is a starch glycolate. A particularly preferred disintegrant is sodium starch glycolate Also preferred are dosage forms including a filler which facilitates the same performance as the disintegrants just described. Most preferably the filler is mannitol.

In a particularly preferred embodiment in accordance with the present invention, there is provided an oral dosage form suitable for buccal, sublingual or gingival administration containing up to about one milligram, and more preferably about ("about" is ±10% by weight when referring to fentanyl) 100, 200, 300, 400, 600, 800 or 1000 micrograms of fentanyl by weight measured as the free base. These formulations further include at least one effervescent couple and in one embodiment, at least one pH adjusting substance and suitable excipient. Preferably such a formulation will be capable of providing a $T_{max}$ of about 1.5 or less and/or a $C_{max}$ between about 2.0 and about 4.0 picograms/mL/microgram. Stated another way the $C_{max}$ of the dosage forms of the present invention are comparable to the $C_{max}$ of an ACTIQ® formulation containing at least about 80 percent more fentanyl by weight.

In another particularly preferred embodiment in accordance with the present invention, there is provided an orally disintegrable tablet suitable for buccal, sublingual or gingival administration containing about 100, 200, 300, 400, 600, 800 or 1000 micrograms of fentanyl measured as the free base, at least one effervescent couple, and at least one pH adjusting substance, as well as suitable disintegrants and/or fillers, said dosage form being capable of providing a $T_{max}$ of less about 1 hour and a $C_{max}$ of between about 2.7 and about 3.5 picograms/mL/microgram.

In yet another embodiment in accordance with the present invention, any of the formulations previously mentioned herein may consist essentially of fentanyl measured as the free base, preferably in an amount of about 1000 micrograms or less, an effervescent couple, at least one pH adjusting substance and suitable excipients which are capable of providing a $T_{max}$ of less than 1.5 hours and most preferably about 1 hour or less, and/or a $C_{max}$ of between about 2.0 and about 4.0 picograms/mL/microgram, more preferably between about 2.5 and about 3.5 picograms/mL/microgram, and most preferably between about 2.7 and about 3.5 picograms/mL/ microgram and containing at least about 45% less fentanyl than an ACTIQ® dosage form providing comparable $C_{max}$. In the present context, "consisting essentially of" is meant to exclude any excipient or combination of excipients or, as appropriate, any amount of any excipient (including disintegrants and fillers in this instance) or combination of excipients, as well as any pH adjusting substance or any amount of pH adjusting substance that would alter the basic and novel characteristics of the invention. Thus, a particular excipient or mixture of for example disintegrants and fillers that would increase the $T_{max}$ to 3 hours or greater would be excluded. Similarly, and again for exemplary purposes only, a combination of excipients provided in a specific amount which would alter $C_{max}$ to a level not contemplated would be excluded. For example, a small amount of cross-linked PVP and/or lactose monohydrate, while generally undesirable, which would not significantly alter the $T_{max}$ or $C_{max}$ of the dosage forms of the invention could still be used. However, if used at levels of 5% and 20% respectively, they can alter the properties adversely. Thus, these amounts of these excipients, in combination, would be excluded.

In another particularly preferred embodiment of this aspect of the present invention, there is provided dosage form consisting essentially of: between about 100 and about 1,000 μg of fentanyl, calculated as fentanyl free base, or a proportionate amount of a salt thereof, sodium starch glycolate, mannitol, at least one pH adjusting substance and at least one effervescent couple. These are all provided in amounts which can provide a $T_{max}$ of 1.5 hours or less or a ratio of $C_{max}$ to dose of between about 2.0 and about 4.0 picograms/mL/ microgram, the dosage form being suitable for buccal, sublingual or gingival administration.

Also contemplated as another aspect of the invention are methods of administering fentanyl to patients experiencing pain in general including but not limited to: back pain, lower back pain, joint pain, any form of arthritic pain, pain from trauma or accidents, neuropathic pain, surgical or postoperative pain, pain from a disease or condition other than cancer, cancer pain and in particular, breakthrough pain as a result of cancer. A preferred method includes the steps of administering to a patient in need thereof any orally disintegrable tablet disclosed herein for buccal, gingival or sublingual administration, which includes a dose of fentanyl of between about 100-1000 micrograms (measured as a free base), preferably a dose of about 100-1000 micrograms, and holding the dosage form in the mouth of the patient for a time sufficient to allow transport of said dose (or a therapeutically significant and/or effective portion thereof) from the oral cavity to the blood stream. Preferably, the patient is instructed, trained or watched to ensure that the dose is not swallowed and instead to the extent practicable, the fentanyl enters the body through one or more of the surfaces within the mouth and oral cavity. The method also preferably includes the step of holding the dosage form in the mouth, substantially without moving it within the oral cavity. In another preferred aspect, the dose dissolves/disintegrates (ceases to be identifiable as a tablet) on average, also referred to herein as a mean dwell time, in between about 5 and about 30 minutes.

One such method is a method of treating episodes of breakthrough cancer pain comprising the steps of providing an initial dose of about 100 micrograms of fentanyl, calculated as a fentanyl free base, or an equivalent amount of a salt thereof. This active is provided in a dosage form comprising an effervescent couple in amount of about 5 to about 85% by weight of the dosage form, a pH adjusting substance in an amount of about 0.5 to about 25% by weight of the dosage form, and a starch glycolate in the amount of 0.25 to about 20% by weight of the dosage form. The dosage form is suitable for delivery of said fentanyl across the oral mucosa of a patient. By "providing" it is understood that removing a dosage form from a package or having someone hand out or dispense such a dosage form are included. The method also includes placing the dosage form in the mouth of the patient between the cheek and the upper or lower gum, for a time sufficient to deliver a therapeutically effective amount of said fentanyl across said oral mucosa. The same method may be employed for the treatment of other types of pain including any type of back pain, surgical or postoperative pain and neuropathic pain.

Based on experience with the ACTIQ product, it would not have been expected that it would be possible to produce an orally disintegrable tablet designed for administration of fentanyl in the oral cavity which was capable of providing $T_{max}$ of about 1.5 hours or less containing 1000 micrograms of fentanyl, measured as free base, or less and having a desirable $C_{max}$. While certain literature for the ACTIQ lozenge suggests a $T_{max}$ of about 45 minutes, testing has shown this to be closer to two hours.

It was not expected that it would be possible to produce an orally disintegrable dosage form designed for administration of fentanyl in the oral cavity through buccal, sublingual or gingival administration route which contained at least about 45% less fentanyl than the ACTIQ® dosage form which provided comparable $C_{max}$ data.

It was also not expected that it would be possible to produce an orally disintegrable dosage form and use it to treat pain, and in particular the breakthrough pain experienced by cancer patients wherein a therapeutically effective amount (an amount which can provide some measure of pain relief) more than 75%, more preferably more than 80% and most preferably 90% or more of the fentanyl dose is absorbed into the blood stream from the oral cavity across the oral mucosa.

In accordance with another aspect of the present invention, there is provided a method of making a buccal, gingival or sublingual, effervescent fentanyl dosage form capable of providing one or more of: a comparable Cmax at a dose of at least about 45% less fentanyl when compared to a non-effervescent formulation such as ACTIQ at the same dose; and a ratio of Cmax to dose of 2.0 to 4.0 picograms/mL/micrograms. This is accomplished by mixing an amount of fentanyl (based on the weight of the free base) of between about 100 to about 1000 micrograms per dosage form with an effective amount of an effervescent couple, an effective amount of a pH adjusting substance capable of producing a change in the localized pH in the microenvironment at the surface contact area of the oral mucosa and the dosage form once placed in the mouth of a patient ("localized pH"), as measured as described herein, of at least 0.5 pH units when compared to an identical formulation without the pH adjusting substance, and a disintegrant which permits the dose reduction, linearity and ratio of Cmax and dose as described above. These are compressed into a tablet or otherwise formed into a dosage form using conventional techniques. Preferably this process is accomplished without granulation, although the individual materials used may be granulated before mixing. Thus, a wet granulated sugar could be used as a filler in an otherwise dry and direct compression process.

More preferably, the method is used to make a dosage form, preferably a tablet, that produces a highly comparable Cmax at a dose of at least about 50% less fentanyl when compared to ACTIQ at the same dose and/or a ratio of Cmax to dose of between about 2.7 and about 3.5 picorgrams/mL/micrograms. This is accomplished by mixing an amount of fentanyl or a salt thereof appropriate to provide a predetermined number of dosage forms each having between about 100 and about 1000 micrograms of fentanyl, an effervescent couple in an amount of about 5 to about 85% by weight of the finished dosage forms (w/w), a pH adjusting substance in an amount of between about 0.5 to about 25% w/w, a starch glycolate in an amount of between about 0.25 and about 20% w/w with or without mannitol, and compressing same into a tablet in a dry state. Preferably, the pH adjusting substance will provide a change in localized pH of at least about 1 pH unit when compared to an identical formulation without same.

DETAILED DESCRIPTION

Throughout the entire specification, including the claims, the word "comprise" and variations of the word, such as "comprising" and "comprises," as well as "have," "having," "includes," "include" and "including," and variations thereof, means that the named steps, elements or materials to which it refers are essential, but other steps, elements or materials may be added and still form a construct with the scope of the claim or disclosure. When recited in describing the invention and in a claim, it means that the invention and what is claimed is considered to what follows and potentially more. These terms, particularly when applied to claims, are inclusive or open-ended and do not exclude additional, unrecited elements or methods steps.

For purposes of the present invention, unless otherwise defined with respect to a specific property, characteristic or variable, the term "substantially" as applied to any criteria, such as a property, characteristic or variable, means to meet the stated criteria in such measure such that one skilled in the art would understand that the benefit to be achieved, or the condition or property value desired is met.

The present invention includes, in one aspect, a dosage form comprising between about 100 and about 1,000 of fentanyl, preferably between about 100 and about 800 micrograms of fentanyl, calculated as fentanyl free base, or a salt thereof, suitable for buccal, sublingual or gingival administration. The dosage form, when properly administered by contacting it to the oral mucosa for a sufficient time, is capable of providing a $T_{max}$ of 1.5 hours or less, more preferably 1.0 hours or less. In addition, or instead, the ratio of $C_{max}$ to dose of between about 2.0 and about 4.0, more preferably between about 2.3 and about 3.5 and most preferably between about 2.7 and about 3.5 picograms/mL/microgram will be realized. The dosage form preferably further comprises at least one pH adjusting substance and at least one effervescent couple. When used, these are each provided in an amount that is sufficient to provide the desired $T_{max}$ and/or $C_{max}$. The dosage form also preferably comprises at least one excipient in an amount which, in combination with the at least one pH adjusting substance and/or the at least one effervescent couple, is sufficient to provide the desired $T_{max}$ and/or $C_{max}$.

A method of administering fentanyl to a patient experiencing pain is another aspect of the invention. This method can comprise the steps of contacting the oral mucosa of a patient in need thereof with an orally disintegrable dosage form. The dosage form includes a dose of fentanyl of about 100-1000 micrograms (measured as a free base), more preferably between about 100 and about 800 micrograms of fentanyl per dosage form, or a corresponding amount of a salt thereof. The dosage form is capable of providing a $T_{max}$ of 1.5 hours or less, more preferably 1.0 hours or less and/or a ratio of $C_{max}$ to dose of between about 2.0 and about 4.0, more preferably between about 2.3 and about 3.5 and most preferably between about 2.7 and about 3.5 picograms/mL/microgram. The dosage form is held in contact with the oral mucosa of the patient for a time sufficient to allow transport of a therapeutically effective portion of the fentanyl, preferably more than 75%, more preferably more than 80% and most preferably 90% or more of the dose, from the oral cavity to the blood stream across the oral mucosa.

Another aspect of the invention provides a dosage form comprising: between about 100 and about 1000 micrograms of fentanyl, calculated as fentanyl free base. A proportionate amount of a fentanyl salt may also be used as long as the corresponding amount of fentanyl free base is provided. These dosage forms are suitable for buccal, sublingual or gingival administration. The dosage form, when properly administered by contacting it to the oral mucosa for a sufficient time, is capable of providing a $C_{max}$ which is at least about 75% to about 125%, more preferably between about 80 and about 120%, and most preferably between about 85% to about 115% that of an ACTIQ® formulation wherein the latter includes at least 80% more fentanyl by weight. This dosage form also includes at least one pH adjusting substance and at least one effervescent couple in an amount which is sufficient to provide the stated $C_{max}$. Even more preferably, the dosage form further comprises at least one excipient in an amount which, in combination with the at least one pH adjusting substance and/or at least one effervescent couple is sufficient to provide the desired $C_{max}$.

There is also contemplated a method of administering fentanyl to a patient experiencing pain comprising the steps of contacting the oral mucosa of a patient in need thereof with an orally disintegrable dosage form which includes a dose of fentanyl of between about 100 and about 1000 micrograms (measured as a free base), more preferably 100-800 micrograms per dosage form, or the equivalent amount of a salt thereof. The dosage form exhibits a $C_{max}$ which is at least about 75% to about 125%, more preferably between about 80 and about 120%, and most preferably between about 85% to about 115% that of an ACTIQ® formulation including at least 80% more fentanyl by weight. The dosage form is held in contact with the oral mucosa of the patient for a time sufficient to allow transport a therapeutically significant or effective portion of the fentanyl, preferably more than 75%, more preferably more than 80% and most preferably 90% or more of the dose, from the oral cavity to the blood stream across the oral mucosa.

It has been discovered that the use of effervescence and/or a pH adjusting substance, and most preferably both, can provide significant advantages particularly in terms of the amount of fentanyl that is required for dosing. It has also been found that certain disintegrants and fillers in combination with at least one effervescent couple and at least one pH adjusting substance can provide even better, and very unexpected, results.

Determining whether or not a particular formulation is capable of achieving the results described herein, one need only undertake a routine human clinical study of that formulation in at least 10 patients. The appropriate clinical study would use any of the traditional models. Examples of appropriate studies follow:

Clinical Study Design and Conduct

This study and Informed Consent Forms (ICF) were Institutional Review Board (IRB) approved. All subjects read and signed an IRB-approved ICF prior to study initiation. Signed and witnessed ICFs are on file.

For the first two periods the study utilized a single-dose, randomized, open-label, 2-way crossover design of the designated test and reference products, and subjects were randomized to receive one of three additional test formulations during Period 3. All subjects were randomized and were in a fasted state following a 10-hour overnight fast. There was a 7-day washout interval between the three dose administrations. The subjects were confined to the clinic through 36 hours post-fentanyl administration.

The subjects were screened within 21 days prior to study enrollment. The screening procedure included medical history, physical examination (height, weight, frame size, vital signs, and ECG), and clinical laboratory tests (hematology, serum chemistry, urinalysis, HIV antibody screen, hepatitis B surface antigen screen, hepatitis C antibody screen, serum pregnancy [females only]), and a screen for cannabinoids and opioids.

All subjects enrolled in the study satisfied the inclusion/exclusion criteria as listed in the protocol. A total of 42 subjects, 17 males and 25 females, were enrolled in the study, and 39 subjects, 17 males and 22 females, completed the study.

Subjects reported to the clinic on the morning prior to each dosing and received lunch 19 hours prior to dosing, dinner 14 hours prior to dosing, and a snack 11 hours prior to dosing. The subjects then observed a 10-hour overnight fast. On Day 1, a standardized meal schedule was initiated with lunch at 4.5 hours postdose, dinner at 9.5 hours postdose, and a snack at 13 hours postdose. On Day 2, breakfast was served at 24.5 hours postdose, lunch at 28.5 hours postdose, and dinner at 33 hours postdose.

The subjects were not to consume any alcohol-, broccoli-, citrus-, caffeine-, or xanthine-containing foods or beverages for 48 hours prior to and during each period of confinement. Subjects were to be nicotine- and tobacco-free for at least 6 months prior to enrolling in the study. In addition, over-the-counter medications were prohibited 7 days prior to dosing and during the study. Prescription medications were not allowed 14 days prior to dosing and during the study (excluding hormonal contraceptives for females).

During the study, the subjects were to remain seated for 4 hours after the fentanyl citrate was administered. Water was restricted from Hour 0 until 4 hours postdose. Food was restricted 10 hours predose until 4 hours postdose. During the study, the subjects were not allowed to engage in any strenuous activity.

Subjects received naltrexone at each period as detailed below:

Adm 1:
ReVia® 50 mg (naltrexone hydrochloride tablets)
Manufactured by Bristol-Myers Squibb Company
Lot No.: 5C269A
Expiration date: April 2004
Lot No.: TB1798
Expiration date: March 2005

Subjects assigned to Treatments A, B, C, and D received an oral dose of one 50 mg naltrexone tablet taken with 240 mL of water at 15 hours and 3 hours prior to and 12 hours following the fentanyl dose.

Subjects assigned to Treatment E received an oral dose of one 50 mg naltrexone tablet taken with 240 mL of water at 15 hours and 3 hours prior to the fentanyl dose.

Subjects received one of the following fentanyl treatments at each of 3 periods:

A:
OraVescent® Fentanyl Citrate Tablets 1080 μg (as fentanyl base)
Manufactured by CIMA LABS INC
Lot No.: 930502

Subjects randomized to Treatment A received a single oral dose of one 1080 μg fentanyl tablet placed between the upper gum and cheek above a molar tooth and allowed to disintegrate for 10 minutes. Note that "OraVescent" indicates a formulation and dosage form in accordance with the present invention.

B:
Actiq® (oral transmucosal fentanyl citrate) equivalent to 1600 μg
Manufactured by Cephalon, Inc. or Anesta
Lot No.: 02 689 W3

Subjects randomized to Treatment B received a single oral dose of one 1600 μg Actiq® unit placed between the cheek and lower gum. The unit was to be moved from side to side using the handle and allowed to dissolve for 15 minutes.

C:
OraVescent® Fentanyl Citrate Tablets 1300 μg (as fentanyl base)
Manufactured by CIMA LABS INC
Lot No.: 930503

Subjects randomized to Treatment C received a single oral dose of one 1300 μg fentanyl tablet placed between the upper gum and cheek above a molar tooth and allowed to disintegrate for 10 minutes.

D:
OraVescent® Fentanyl Citrate Tablets 810 μg (as fentanyl base)
Manufactured by CIMA LABS INC
Lot No.: 930501

Subjects randomized to Treatment D received a single oral dose of one 810 μg fentanyl tablet placed between the upper gum and cheek above a molar tooth and allowed to disintegrate for 10 minutes.

E:
OraVescent® Fentanyl Citrate Tablets 270 μg (as fentanyl base)
Manufactured by CIMA LABS INC
Lot No.: 930500

Subjects randomized to Treatment E received a single oral dose of one 270 μg fentanyl tablet placed between the upper gum and cheek above a molar tooth and allowed to disintegrate for 10 minutes.

The composition of each of these fentanyl citrate tablets is described in Examples 1-4.

Sitting vital signs (blood pressure, pulse, and respiration) were assessed each morning prior to dosing (Hour 0) and at 0.25, 0.5, 0.75, 1, 1.25, 1.5, 1.75, 2, 2.25, 2.5, 2.75, 3, 3.25, 3.5, 3.75, 4, 5, 6, 8, 10, 24, and 36 hours postdose. Continuous pulse oximetry was conducted for the first 8 hours postdose. A 12-lead electrocardiogram, a clinical laboratory evaluation (hematology, serum chemistry, and urinalysis), and a physical examination with complete vital signs were performed at the completion of the study. Oral irritation assessments were conducted 4 hours postdose. Subjects were instructed to inform the study physician and/or nurses of any adverse events that occurred during the study.

Blood samples (7 mL) were collected at the following times for subjects assigned to Treatments A-D: predose (Hour 0), and 10, 20, 30, and 45 minutes; and 1, 2, 4, 6, 8, 10, 12, 16, 20, 24, 28, 32, and 36 hours postdose. Blood samples (7 mL) were collected at the following times for subjects assigned to Treatment E: predose (Hour 0), and 10, 20, 30, and 45 minutes; and 1, 2, 4, 6, 8, 9, 10, 11, 12, 14, 16, 20, and 24 hours postdose. A total of 54 blood samples (378 mL) were drawn during the study for drug analysis. Samples were collected and processed at room temperature under fluorescent lighting. Serum samples were allowed to clot, separated by centrifugation, frozen at −20° C., and kept frozen until assayed.

Analytical Methods

An LC-MS/MS (liquid chromatography-mass spectrometry/mass spectrometry) of fentanyl in human serum.

Pharmacokinetic and Statistical Methods

The pharmacokinetic and statistical analysis was based on the Food and Drug Administration, Center for Drug Evaluation and Research (CDER), Guidance for Industry issued January 2001 and entitled "Statistical Approaches to Establishing Bioequivalence," and Guidance for Industry issued March 2003 and entitled "Bioavailability and Bioequivalence Studies for Orally Administered Drug Products—General Considerations."

The following noncompartmental pharmacokinetic parameters were computed from the fentanyl concentration-time data for each treatment using WinNonlin Standard Edition version 2.1. Actual (rather than nominal) sampling times were used in the analysis.

| | |
|---|---|
| AUC(0-t) | Area under the fentanyl concentration-time curve calculated using linear trapezoidal summation from time zero to time t, where t is the time of the last measurable concentration (Ct). |
| AUC(0-inf) | Area under the fentanyl concentration-time curve from time zero to infinity, AUC(0-inf) = AUC(0-t) + Ct/Kel, where Kel is the terminal elimination rate constant. |
| AUC(0-t)/AUC(0-inf) | Ratio of AUC(0-t) to AUC(0-inf). Also referred to as AUCR. |
| AUC(0-tmax) | The partial area from time 0 to the median Tmax of the reference formulation, calculated using linear trapezoidal summation. |
| Kel | Terminal elimination rate constant calculated by linear regression of the terminal linear portion of the log concentration vs. time curve, where Kel = −slope. The terminal linear portion was determined by visual inspection. |
| T½ | Elimination half-life calculated as ln(2)/Kel. |
| $C_{max}$ | Maximum observed fentanyl concentration. |
| $T_{max}$ | Time of the maximum fentanyl concentration (obtained without interpolation). |

This study was a single-dose, randomized, open-label, 2-way crossover of the designated test and reference products. (Treatment A and Treatment B, Periods 1 and 2) with subjects randomized to receive one of three additional test formulations (Treatment C, Treatment D, or Treatment E) during Period 3. Due to the larger number of subjects, the study was run in two groups. The primary comparison in this study was Treatment A versus Treatment B. For the analysis of variance comparing these two treatments, only two sequences (AB, BA), two periods (1, 2), and two treatments (A, B) were considered.

A parametric (normal-theory) general linear model was applied to the log-transformed AUC(0-inf), AUC(0-t), and Cmax values from Treatments A and B.[5-7] The full analysis of variance (ANOVA) model considered group in the model and included the following factors: group, period within group, treatment, sequence, sequence by group, subject within sequence by group, and treatment by group. Since the treatment by group interaction was not significant, the model was reduced to sequence, subject within sequence, period, and treatment. The sequence effect was tested using the subject within sequence mean square and all other main effects were tested using the residual error (error mean square). The two one-sided hypotheses were tested at the 5% level for AUC(0-t), AUC(0-inf), and Cmax by constructing 90% confidence intervals for the ratio of the test and reference means (Treatment A versus Treatment B).

Differences in Tmax for Treatment A and Treatment B were evaluated using the Wilcoxon Signed Ranks Test ($\alpha$=0.05).

Serum fentanyl concentrations and pharmacokinetic parameters were also determined following Treatment C, Treatment D, and Treatment E (1300 µg, 810 µg, and 270 µg OraVescent® Fentanyl Citrate tablet, respectively). In order to evaluate dose proportionality of the OraVescent® Fentanyl Citrate formulation, a mixed linear model was applied to the dose-normalized Cmax and AUC parameters from Treatments A, C, D, and E.[5-7] The full model considered group and included the following terms: group, period within group, treatment, sequence, sequence by group, subject within sequence by group, and treatment by group. The treatment by group interaction was not significant for 2 of the 3 parameters [Cmax and AUC(0-t)] and the model was reduced to a one-way ANOVA with the factor of treatment. If an overall treatment effect was found, pairwise comparisons were performed using Treatment A as the reference.

The dwell time values (length of time the formulation was present in the oral cavity) were calculated by subtracting the treatment administration time from the time of perceived and documented disappearance of the formulation. These values were tabulated and summary statistics were presented.

Results

Demographics and Disposition of Subjects

A total of 42 subjects, 17 males and 25 females, were enrolled in the study, and 39 subjects, 17 males and 22 females, completed the study.

Three subjects were discontinued/withdrawn from the study. One subject was dropped prior to Period 2 because the subject did not want to continue on the study. A second subject was dropped prior to Period 3 because the subject did not want to continue on the study. A third subject was dropped prior to Period 2 because subject took an antibiotic.

The mean age of the subjects was 27 years (range 19-55 years), the mean height of the subjects was 68 inches (range 62-74 inches), and the mean weight of the subjects was 152.1 pounds (range 109.0-197.0 pounds).

Protocol Deviations and Adverse Events

The following protocol deviations occurred during the conduct of the study.

According to the protocol, subjects were to have respirations taken at the 3.5-hour vital signs time point. Respirations were not taken at the 3.5-hour time point for one subject during Period 2. Vital sign recheck was not performed at the 3-hour time point of Period 2 for two subjects. Vital sign recheck was not performed at the 2.25-hour time point of Period 3 for one subject. The blood samples for these two subjects were not labeled properly at the 0.33-hour time point of Period 1 (Treatment A). These samples were not analyzed. According to the protocol, subjects were to have pulse taken at the 3.5-hour vital signs time point. Pulse was not taken at the 3.5-hour time point for one subject during Period 1. No one subject was exposed to more than one of the foregoing deviations. No serious adverse events were reported.

A total of 15 batches were required to process the clinical samples from this study. Of these 15 batches, 14 were acceptable. Back-calculated standard concentrations for the 14 acceptable batches for human serum used in this study covered a range of 50.0 to 5000.0 (pecograms/mL) pg/mL with a limit of quantitation of 50.0 pg/mL. Quality control samples analyzed with each acceptable batch had coefficients of variation less than or equal to 7.89%.

Dwell Time

The dwell time data are summarized in the table below.

| | | | Summary of Tablet/Lozenge Dwell Time | | |
|---|---|---|---|---|---|
| Subject Number | Treatment A Time (Minutes) | Treatment B Time (Minutes) | Treatment C Time (Minutes) | Treatment D Time (Minutes) | Treatment E Time (Minutes |
| Mean | 21 | 34 | 19 | 25 | 22 |
| SD | 12 | 15 | 11 | 14 | 17 |
| CV | 58 | 44 | 56 | 57 | 75 |
| SEM | 2 | 2 | 3 | 4 | 4 |
| N | 40 | 42 | 12 | 13 | 14 |
| Minimum | 3 | 9 | 4 | 4 | 4 |
| Maximum | 48 | 77 | 33 | 50 | 62 |

Treatment A = 1 × 1080 mcg OraVescent Fentanyl Citrate Tablet: test
Treatment B = 1 × 1600 mcg Oral Transmucosal Fentanyl Citrate (Actiq): reference
Treatment C = 1 × 1300 mcg OraVescent Fentanyl Citrate Tablet: test
Treatment D = 1 × 810 mcg OraVescent Fentanyl Citrate Tablet: test
Treatment E = 1 × 270 mcg OraVescent Fentanyl Citrate Tablet: test
SD = standard deviation;
CV = coefficient of variance;
SEM = standard error of the mean;
N = number (of observations)

One subject reported slight oral irritation (2 on a scale of 1 to 10) that occurred following Treatment C. The irritation was on the right side of the mouth following test product administration during Period 3. There was one report of redness upon visual inspection of the area by study personnel that occurred following Treatment E. The redness was on the right upper cheek following test product administration during Period 3.

Of the 42 subjects enrolled, 40 subjects completed Periods 1 and 2 and were included in the summary statistics, ANOVA analysis, and mean figures for Treatments A and B. Thirty-nine subjects completed Periods 1, 2, and 3 and were included in the statistical analysis for dose proportionality.

The arithmetic means and standard deviations of the serum fentanyl pharmacokinetic parameters and statistical comparisons following Treatment A and Treatment B are summarized in the following table.

| | | Summary of the Pharmacokinetic Parameters of Serum Fentanyl for Treatments A and B | | | | | | |
|---|---|---|---|---|---|---|---|---|
| | | | Serum Fentanyl | | | | | |
| | | Treatment A | | | Treatment B | | | |
| Pharmacokinetic Parameters | N | Arithmetic Mean | SD | N | Arithmetic Mean | SD | 90% CI* | % Mean Ratio |
| Cmax (pg/mL) | 40 | 2704.3 | 877.6 | 40 | 2191.6 | 693.5 | — | — |
| AUC(0-tmax) (pg * hr/mL) | 40 | 3840.1 | 1266.2 | 40 | 2566.2 | 911.82 | — | — |
| AUC(0-t) (pg * hr/mL) | 40 | 16537 | 5464.6 | 40 | 16701 | 6530.1 | — | — |
| AUC(0-inf) (pg * hr/mL) | 35 | 17736 | 5424.3 | 39 | 18319 | 7118.5 | — | — |
| T½(hr) | 35 | 11.7 | 5.04 | 39 | 11.2 | 4.37 | — | — |
| Kel(1/hr) | 35 | 0.0701 | 0.0310 | 39 | 0.0695 | 0.0227 | — | — |
| AUCR | 35 | 0.918 | 0.0458 | 39 | 0.917 | 0.0335 | — | — |
| ln(Cmax) | 40 | 7.854 | 0.3132 | 40 | 7.640 | 0.3349 | 111.82-136.20 | 123.4 |
| ln[AUC(0-t)] | 40 | 9.662 | 0.3226 | 40 | 9.649 | 0.3945 | 94.42-108.86 | 101.4 |
| ln[AUC(0-inf)] | 35 | 9.739 | 0.3027 | 39 | 9.742 | 0.3941 | 93.60-109.23 | 101.1 |

Treatment A = 1 × 1080 mcg OraVescent Fentanyl Citrate Tablet: test
Treatment B = 1 × 1600 mcg oral Transmucosal Fentanyl Citrate (Actiq): reference Results of the Wilcoxon Signed Rank Test showed the median Tmax for Treatment A (0.998 hour) was significantly earlier (p<0.0001) compared to Treatment B (1.999 hours).

The individual and mean serum fentanyl pharmacokinetic parameters for Treatments C, D, and E were calculated. There were 5 subjects in Treatment E for whom Kel could not be calculated. Thus, AUC(0-inf), AUCR, and T1/2 could not be calculated in these cases.

The arithmetic mean and standard deviations of the serum fentanyl pharmacokinetic parameters following Treatments C, D, and E are summarized in the following table.

2-way crossover design for Periods 1 and 2. All subjects also returned in Period 3 for administration of one of three OraVescent® Fentanyl Citrate test formulations: 1300 μg (Treatment C), 810 μg (Treatment D), or 270 μg (Treatment E). Dose-proportionality of the OraVescent® Fentanyl Citrate tablet formulation (Treatments A, C, D, and E) was evaluated.

A total of 42 healthy subjects were initially enrolled in the study. 39 subjects completed all three periods of the study, and 40 subjects completed both Treatments A and B (Periods Summary of the Pharmacokinetic Parameters of Serum Fentanyl for Treatments C, D, and E

| | Serum Fentanyl | | | | | | | | |
|---|---|---|---|---|---|---|---|---|---|
| | Treatment C | | | Treatment D | | | Treatment E | | |
| Pharmacokinetic Parameters | N | Arithmetic Mean | SD | N | Arithmetic Mean | SD | N | Arithmetic Mean | SD |
| Cmax(pg/mL) | 12 | 2791.4 | 874.3 | 13 | 2646.9 | 778.7 | 14 | 797.9 | 312.9 |
| AUC(0-tmax) (pg * hr/mL) | 12 | 4008.3 | 1259.1 | 13 | 3694.8 | 971.89 | 14 | 1095.6 | 433.92 |
| AUC(0-t) (pg * hr/mL) | 12 | 18921 | 6470.2 | 13 | 15339 | 4260.4 | 14 | 4333.5 | 1597.9 |
| AUC(0-inf) (pg * hr/mL) | 12 | 21033 | 7346.3 | 13 | 16831 | 4449.8 | 9 | 4221.9 | 1747.8 |
| T½(Hr) | 12 | 13.2 | 7.67 | 13 | 11.7 | 4.66 | 9 | 6.62 | 3.17 |
| Kel(1/hr) | 12 | 0.0687 | 0.0354 | 13 | 0.0703 | 0.0352 | 9 | 0.126 | 0.0538 |
| AUCR | 12 | 0.907 | 0.0683 | 13 | 0.909 | 0.0376 | 9 | 0.865 | 0.0381 |

Treatment C = 1 × 1300 mcg OraVescent Fentanyl Citrate Tablet
Treatment D = 1 × 810 mcg OraVescent Fentanyl Citrate Tablet
Treatment E = 1 × 270 mcg OraVescent Fentanyl Citrate Tablet
AUCR is ratio of $AUC_{0-t}/AUC_{0-\infty}$ The dose proportionality assessment including p-values for Treatments A, C, D, and E are summarized in the following table.

1 and 2). Data from the 40 subjects completing Treatments A and B were included in the pharmacokinetic and statistical analysis.

Summary of the Dose-Normalized Parameters of Serum Fentanyl for Treatments A, C, D and E

| | | Serum Fentanyl | | | | | | | |
|---|---|---|---|---|---|---|---|---|---|
| | | Treatment A | | Treatment C | | Treatment D | | Treatment E | |
| Pharmacokinetic Parameters | P-Value | Arithmetic Mean | SD | Arithmetic Mean | SD | Arithmetic Mean | SD | Arithmetic Mean | SD |
| Cmax/dose (pg/mL/mcg) | — | 2.5 | 0.8 | 2.1 | 0.7 | 3.3 | 1.0 | 3.0 | 1.2 |
| AUC(0-t)/dose (pg * hr/mL/mcg) | — | 15.4743 | 5.01901 | 14.555 | 4.9771 | 18.937 | 5.2597 | 16.050 | 5.9180 |
| AUC(0-inf)/dose (pg * hr/mL/mcg | — | 16.5851 | 5.00318 | 16.179 | 5.6510 | 20.779 | 5.4935 | 15.637 | 6.4732 |
| ln(Cmax/dose) | 0.0127 | 0.8788 | 0.3115 | 0.7190 | 0.3151 | 1.137 | 0.3356 | 1.011 | 0.3974 |
| Ln[AUC(0-t)/dose] | 0.1727 | 2.690 | 0.3170 | 2.625 | 0.3409 | 2.901 | 0.3032 | 2.706 | 0.4002 |
| ln[AUC(0-inf)/dose] | 0.0783 | 2.765 | 0.3003 | 2.725 | 0.3633 | 2.998 | 0.2894 | 2.691 | 0.3892 |

Treatment A = 1 × 1080 mcg OraVescent Fentanyl Citrate Tablet
Treatment C = 1 × 1300 mcg OraVescent Fentanyl Citrate Tablet
Treatment D = 1 × 810 mcg OraVescent Fentanyl Citrate Tablet
Treatment E = 1 × 270 mcg OraVescent Fentanyl Citrate Tablet The time intervals over Kel values were determined.

The primary objective of this study was to assess the bioequivalence of a 1080 μg dose of CIMA LABS INC OraVescent® Fentanyl Citrate tablet (Treatment A, test) compared to a marketed 1600 μg oral transmucosal fentanyl citrate, Actiq® (Treatment B, reference) under fasted conditions. The study was a single-dose randomized, open-label, The ratios of geometric least square means (test/reference) for fentanyl Cmax, AUC(0-t), and AUC(0-inf) were 123.4%, 101.4%, and 101.1%, respectively, for Treatment A versus Treatment B. These data indicate that the average fentanyl exposure was similar but the peak exposure was higher for Treatment A compared to Treatment B. The Tmax for Treatment A (0.998 hour) occurred an hour earlier than Treatment B (2.00 hour) and Cmax was 23% higher, indicating that the rate of fentanyl absorption was significantly faster for Treatment A compared to Treatment B.

The 90% confidence intervals for Cmax at 111.82%-136.20%, AUC(0-t) at 94.42%-108.86%, and AUC(0-inf) at 93.60%-109.23% indicated that Treatment A and Treatment B met the requirements for bioequivalence with respect to AUC but not with respect to Cmax. In fact, the Cmax of Treatment A indicates that a dose of about 30-35% less fentanyl by weight given using the OraVescent® formulation exemplified in Example 1 provided a statistically significantly higher Cmax when compared to a 1600 microgram Actiq® formulation. To obtain bioequivalent results in terms of Cmax, indeed to obtain comparable results, one would have to use an OraVescent® fentanyl formulation including at least about 45%, more preferably about 47.5% and even more preferably about 50% less fentanyl (calculated as free fentanyl by weight) than found in the comparator Actiq® tablet. In this instance, approximately 800-880 micrograms was comparable to a 1600 microgram ACTIQ.

Thus it was discovered that, using the present invention and for dosage forms of 1 milligram or less, one could obtain comparable $C_{max}$ with even less fentanyl than initially thought. Rapid $T_{max}$ was also realized. This allowed a further reduction in the doses contemplated with the advantages described previously herein that come from a dose reduction that is not coupled with a reduction in efficacy.

Fentanyl AUC increased proportionally to the dose in the range of 270 to 1300 µg following administration of the OraVescent® Fentanyl Citrate tablet formulation. There were no significant differences in dose-normalized AUC(0-t) or AUC(0-inf) among the 4 OraVescent® doses. A significant overall treatment effect was found for the comparison of dose-normalized Cmax. Pairwise comparisons were performed using Treatment A as the reference because all subjects received Treatment A. No pattern was observed with the pairwise comparisons. A significant difference between Treatment D (810 µg) and Treatment A (1080 µg) was found.

The mean dwell time of the 1080 µg OraVescent® Fentanyl Citrate tablet (21 minutes) was 13 minutes shorter than for Actiq® (34 minutes). Mean dwell times for the other 3 doses of the OraVescent® Fentanyl Citrate tablet formulation (19, 25, and 22 minutes) were similar to 1080 µg OraVescent® formulation.

One subject reported minor irritation to the oral mucosa, and one subject experienced redness following the OraVescent® Fentanyl Citrate tablet. There was no irritation or redness reported following Actiq®.

Comparison of serum fentanyl pharmacokinetics following the administration of 1080 µg OraVescent® Fentanyl Citrate tablet and 1600 µg oral transmucosal fentanyl citrate (Actiq®) showed that the average fentanyl exposure was similar but the rate of absorption was different between the two products. The geometric least squared (LS) mean ratios for AUC(0-t) and AUC(0-inf) were near 100%, and 90% confidence intervals were within 80% to 125%. Geometric LS mean Cmax was 23% higher for 1080 µg OraVescent® Fentanyl Citrate, and the upper limit of the 90% confidence interval for the treatment/reference ratio was greater than 125%, indicating that bioequivalence criteria were not met for this parameter. Thus even further dose reduction could be realized. The Tmax was significantly earlier (1 hour earlier) for the OraVescent® Fentanyl Citrate tablet.

Fentanyl AUC increased proportionally to the dose in the range of 270 to 1300 µg for the OraVescent® Fentanyl Citrate formulation.

The mean dwell time for the 1080 µg OraVescent® Fentanyl Citrate tablet (21 minutes) was 13 minutes shorter than the mean dwell time for Actiq® (34 minutes).

There were no serious or unexpected adverse events during the study. Both formulations were well tolerated by the oral mucosa.

REFERENCES

1. Physician's Desk Reference. 56th ed. Montvale, N.J.: Medical Economics Company, Inc.; 2002. Actiq®; p. 405-409.
2. Fentanyl. Micromedex [online] Vol. 107: Health Series Integrated Index; 2002 [Date Accessed: 2003/June/371. http://www.tomescps.com
3. Streisand Y B, et al. Dose Proportionality and Pharmacokinetics of Oral Transmucosal Fentanyl Citrate. Anesthesiology 88:305-309, 1998.
4. Naltrexone. Micromedex [online] Vol. 107: Health Series Integrated Index; 2002 [Date Accessed: 2003/Jun16]. http://www.tomescps.com
5. SAS Institute, Inc., SAS®/STAT User's guide, Ver. 6. 4th ed. Vol. 1. Cary, N.C.: SAS Institute; 1989.
6. SAS Institute, Inc., SAS®/STAT User's guide, Ver. 6, 4th ed. Vol. 2. Cary, N.C.: SAS Institute; 1989.
7. SAS Institute, Inc., SAS® Procedures guide, Ver. 6, 3rd ed. Cary, N.C.: SAS Institute; 1990.

A second study was performed as well.

This study was conducted to evaluate the extent to which dose proportionality (AUC and Cmax) exists for fentanyl citrate formulated in tablets in accordance with the invention (referred to herein as OraVescent® tablets) over the range that may be used therapeutically, and to confirm the Cmax observations of the study just discussed.

An Institutional Review Board (IRB) approved the protocol and the Informed Consent Form. All subjects read and signed an IRB-approved ICF prior to study initiation. This study had a single-dose, randomized, open-label, 4-treatment, 4-period, crossover design.

The subjects were screened within 21 days prior to study enrollment. The screening procedure included medical history, physical examination (height, weight, frame size, vital signs, and electrocardiogram [ECG]), and clinical laboratory tests (hematology, serum chemistry, urinalysis, HIV antibody screen, hepatitis A antibody screen, hepatitis B surface antigen screen, hepatitis C antibody screen, and serum pregnancy [females only]), and a screen for cannabinoids and opiates.

All subjects enrolled in the study satisfied the inclusion/exclusion criteria as listed in the protocol and the Principal Investigator reviewed medical histories, clinical laboratory evaluations, and performed physical examinations prior to subjects being enrolled in the study. A total of 28 subjects, 16 males and 12 females, were enrolled in the study, and 25 subjects, 14 males and 11 females, completed the study.

Subjects reported to the clinic on the afternoon prior to dosing and received lunch at 1400, dinner at 1900, and a snack at 2200. The subjects then observed a 10-hour overnight fast. On Day 1, a standardized meal schedule was initiated with lunch at 1330, dinner at 1830, and a snack at 2200. On Day 2, a standardized meal schedule (including breakfast) was initiated.

The subjects were not to consume any alcohol, broccoli, caffeine-, or xanthine-containing foods or beverages for 48 hours prior to and during each period of confinement. Grapefruit was restricted 10 days prior to dosing and throughout the study. Subjects were to be nicotine- and tobacco-free for at least 6 months prior to and throughout the completion of the study. In addition, over-the-counter medications (including herbal supplements) were prohibited 7 days prior to dosing and during the study. Prescription medications (including MAO inhibitors) were not allowed 14 days prior to dosing and during the study.

During the study, subjects were to remain in an upright position, sitting, for 4 hours after the fentanyl citrate was administered. Water was restricted from the time of dosing until 4 hours postdose. Food was restricted 10 hours predose until 4 hours postdose. During the study, the subjects were not allowed to engage in any strenuous activity.

Subjects were randomized to receive the following treatments:

Adm1:
- ReVia® (naltrexone hydrochloride tablets) 50 mg
- Manufactured by Duramed Pharmaceuticals, Inc.
- Lot No.: 402753001T
- Expiration date: June 2006

Subjects received an oral dose of one ReVia® 50 mg tablet taken with 240 mL of water 15 hours and 3 hours prior to dosing for Treatment A.

Subjects received an oral dose of one ReVia® 50 mg tablet taken with 240 ml. of water 15 hours and 3 hours prior to dosing, and 12.17 hours postdose for Treatment B, C, and D.

A:
- Oravescent® Fentanyl Citrate 200 µg tablets
- Manufactured by CIMA LABS INC
- Lot No.: 930859

Subjects randomized to Treatment A received a single oral dose of one Oravescent® Fentanyl Citrate 200 µg tablet placed between the upper gum and cheek, above a molar tooth, and allowed to disintegrate for 10 minutes.

B:
- Oravescent® Fentanyl Citrate 500 µg tablets
- Manufactured by CIMA LABS INC
- Lot No.: 930860

Subjects randomized to Treatment B received a single oral dose of one Oravescent® Fentanyl Citrate 500 µg tablet placed between the upper gum and cheek, above a molar tooth, and allowed to disintegrate for 10 minutes.

C:
- Oravescent® Fentanyl Citrate 810 µg tablets
- Manufactured by CIMA LABS INC
- Lot No.: 930501

Subjects randomized to Treatment C received a single oral dose of one Oravescent® Fentanyl Citrate 810 µg tablet placed between the upper gum and cheek, above a molar tooth, and allowed to disintegrate for 10 minutes.

D:
- Oravescent® Fentanyl Citrate 1080 µg tablets
- Manufactured by CIMA LABS INC
- Lot No.: 930502

Subjects randomized to Treatment D received a single oral dose of one Oravescent® Fentanyl Citrate 1080 µg tablet placed between the upper gum and cheek, above a molar tooth, and allowed to disintegrate for 10 minutes.

Sitting vital signs (blood pressure, heart rate, and respiratory rate) were assessed each morning prior to dosing and at 0.25, 0.5, 0.75, 1, 1.25, 1.5, 1.75, 2, 2.25, 2.5, 2.75, 3, 3.25, 3.5, 3.75, 4, 5, 6, 8, 10, 24, and 36 hours postdose. Continuous pulse oximetry was obtained for the first 8 hours postdose and whenever the subject attempted to sleep during the first 12 hours postdose. A 12-lead ECG, a clinical laboratory evaluation (hematology, serum chemistry, and urinalysis) and a brief physical examination with complete vital signs were performed at the completion of the study. Oral irritation assessments were conducted 4 hours postdose. At each check-in, the oral cavity was examined to ensure that the subjects did not have canker sores in the area of drug application. Subjects were instructed to inform the study physician or nurses of any adverse events that occurred during the study.

Blood samples (7 mL) were collected at the following times for subjects assigned to Treatment A: Predose (Hour 0), 10, 20, 30, and 45 minutes; and 1, 2, 4, 6, 8, 9, 10, 11, 12, 14, 16, 20, and 24 hours postdose. Blood samples (7 mL) were collected at the following times for subjects assigned to Treatments B, C and D: Predose (Hour 0), 10, 20, 30, and 45 minutes; and 1, 2, 4, 6, 8, 10, 12, 16, 20, 24, 28, 32, and 36 hours postdose.

Human serum samples were analyzed for fentanyl concentrations by a sensitive and specific LC-MS/MS procedure.

The following noncompartmental pharmacokinetic parameters were computed from the fentanyl concentration-time data for each treatment using WinNonlin Standard Edition version 2.1. Actual (rather than nominal) sampling times were used in the analysis.

| | |
|---|---|
| AUC(0-t) | Area under the fentanyl concentration-time curve calculated using linear trapezoidal summation from time zero to time t, where t is the time of the last measurable concentration (Ct). |
| AUC(0-inf) | Area under the fentanyl concentration-time curve from time zero to infinity, AUC(0-inf) = AUC(0-t) ± Ct/Kel, where Kel is the terminal elimination rate constant. |
| AUC(0-t)/AUC(0-inf) | Ratio of AUC(0-t) to AUC(0-inf). Also referred to as AUCR. Kel Terminal elimination rate constant calculated by linear regression of the terminal linear portion of the log concentration vs. time curve, where Kel = –slope. The terminal linear portion was determined by visual inspection. |
| T½ | Elimination half-life calculated as ln(2)/Kel. |
| Cmax | Maximum observed fentanyl concentration. |
| Tmax | Time of the maximum fentanyl concentration (obtained without interpolation). |

Plasma concentration values for fentanyl were listed and summarized by treatment and time point with descriptive statistics (mean, standard deviation [SD], coefficient of variation [CV], standard error of the mean [SEM], sample size, minimum, maximum, and median).[9-11] Values below the lower limit of quantification (LOQ) were set to zero. Mean and individual concentration-time plots were presented. Fentanyl pharmacokinetic parameters and dose-normalized pharmacokinetic parameters were tabulated by treatment and summary statistics were calculated.

Dose proportionality from 200 µg to 1080 µg was assessed using the methodology described by Smith et al.[8] First, log-transformed parameters were analyzed using a mixed effects model including the log-transformation of dose as well as fixed and random effects for intercept. This model was fit using SAS Proc Mixed.[9-11]

A 90% confidence interval (CI) about the fixed effect for slope ($\beta_1$) was calculated and compared to the range (0.8677, 1.1323), which is the appropriate critical range given the range of doses investigated in this study. Conclusions were based on the following:

1) If the 90% CI for $\beta_1$ was entirely contained within the range (0.8677, 1.1323), dose proportionality was to be concluded.
2) If the 90% CI for $\beta_1$ was completely outside this range, lack of dose proportionality was to be concluded.

3) If the 90% CI for $\beta_1$ was partially in and partially outside this range, the results would be considered "inconclusive." In this case, the value of $\beta_1$ as the best estimate of deviation from ideal proportionality, and the lower and upper bounds of the 90% CI may be considered in the context of drug safety, efficacy, or pharmacological effect data.[8]

In the event that inconclusive results were observed, the maximal dose ratio such that the 90% CI for $\beta_1$ lay entirely within the critical range and the dose ratio such that the 90% CI for $\beta_1$ fell entirely outside the critical range were calculated. These dose ratios are referred to by Smith et al., as $\rho 1$ and $\rho 2$, respectively.

$\rho_1 = \theta_H [l/\max(l-L, U-l)]$, where $\theta_H = 1.25$,
L=the lower limit of the 90% CI,
U=the upper limit of the 90% CI.
$\rho_2 = \theta_H [l/\max(L-l, 1-U)]$, with $\theta_H$, L, and U and defined as above.

A secondary analysis to examine the difference in dose-normalized Cmax between the 3 lowest dose levels (200 μg, 500 μg, and 810 μg) was performed. A parametric (normal-theory) GLM was applied to the dose-normalized Cmax values from Treatments A, B, and C following log-transformation. The analysis of variance (ANOVA) model included the following factors: treatment, sequence, subject within sequence and period. A p-value less than 0.05 was considered statistically significant.

The dwell time values (length of time the formulation was present in the oral cavity) were calculated by subtracting the medication administration time from the time of perceived and documented disappearance of the formulation. These values were tabulated and summary statistics were presented.

Three subjects were discontinued/withdrawn from the study. Two were dropped prior to Period 3 because they did not want to continue on the study. One subject was dropped following dosing on Period 2 because of adverse events. The mean age of the subjects was 33 years (range 19-55 years), the mean height of the subjects was 68.6 inches (range 60-76 inches), and the mean weight of the subjects was 160.9 pounds (range 110-215 pounds).

The following protocol deviations occurred during the conduct of the study. A vital sign recheck was not performed at Hour 0.5 of Period 2 for one subject. A vital sign recheck was not performed at Hour 2.5 of Period 3 for one subject. One subject did not have her serum pregnancy test result available prior to the −15-hour naltrexone dosing on Period 3. The result was made available prior to the −3-hour naltrexone dose. The ECG for Hour 36 of Period 4 was misplaced for one subject. One subject did not have early termination procedures completed. This subject is considered lost to follow-up.

And, for all subjects during Period 3, an oral irritation assessment was to have been conducted at 3.83 hours postdose. The nurse responsible for the event recalled performing the assessments but stated that the oral irritation assessment forms were not completed at the time of the event. Therefore, the assessment information cannot be verified and should be considered not done.

The dwell time data are summarized in the table below.

| Subject Number | Treatment A Time (Minutes) | Treatment B Time (Minutes) | Treatment C Time (Minutes) | Treatment D Time (Minutes) |
|---|---|---|---|---|
| MEAN | 14 | 14 | 17 | 15 |
| SD | 8 | 6 | 10 | 11 |
| CV | 59 | 45 | 57 | 72 |
| SEM | 2 | 1 | 2 | 2 |
| N | 25 | 26 | 27 | 27 |
| Minimum | 4 | 6 | 5 | 4 |
| Maximum | 37 | 33 | 41 | 60 |

Treatment A = 200 μg
Treatment B = 500 μg
Treatment C = 810 μg
Treatment D = 1080 μg During the check-in oral cavity assessments it was noted that one subject had a canker sore on the lower right inner cheek at the beginning of Period 4, however, the test product administration during Period 3 occurred on the upper right cheek. The Principal Investigator identified this canker sore as not an apthous ulcer and approved the subject to dose during Period 4.

Two subjects reported slight oral irritation (2 and 3 on a scale of 1 to 10) that occurred following Treatment A. The irritation was on the left side of the mouth following test product administration during Period 2 for both subjects; one of these subjects also exhibited redness upon visual inspection of the area by study personnel. One additional subject reported pain in the upper left buccal area at the gum line 11 minutes following Treatment C. No serious or unexpected adverse events were reported.

Of the 28 subjects enrolled, 25 subjects completed Treatment A, 26 subjects completed Treatment B, and 27 subjects completed Treatments C and D. Statistical analysis was performed on the pharmacokinetic data for all subjects. The elimination rate constant could not be calculated in one subject in Treatment A because there were limited data points in the terminal phase. Thus, AUC(0-inf), AUCR, and T1/2 could not be calculated for this subject.

The arithmetic means and standard deviations of the serum fentanyl pharmacokinetic parameters following all treatments are summarized in the following table.

Summary of the Pharmacokinetic Parameters of Serum Fentanyl

| | SERUM FENTANYL | | | | | | | | | | | |
|---|---|---|---|---|---|---|---|---|---|---|---|---|
| | Treatment A | | | Treatment B | | | Treatment C | | | Treatment D | | |
| Pharmacokinetic Parameters | N | Arithmetic Mean | SD | N | Arithmetic Mean | SD | N | Arithmetic Mean | SD | N | Arithmetic Mean | SD |
| $C_{max}$ (pg/mL) | 25 | 617.8 | 236.7 | 26 | 1546.2 | 621.4 | 27 | 2280.1 | 968.9 | 27 | 2682.3 | 1106.0 |
| *$T_{max}$ (hr) | 25 | 0.76 | 0.33-4.0 | 26 | 0.75 | 0.33-4.0 | 27 | 0.99 | 0.33-4.0 | 27 | 0.75 | 0.33-4.0 |
| AUC(0-t) (pg * hr/mL) | 25 | 2876.3 | 1107.7 | 26 | 8501.2 | 3346.2 | 27 | 13301 | 4069.1 | 27 | 16813 | 5232.2 |
| AUC(0-inf) (pg * hr/mL) | 24 | 3543.9 | 1304.5 | 26 | 9701.9 | 2651.5 | 27 | 14962 | 4709.6 | 27 | 18664 | 6266.0 |

-continued

Summary of the Phamacokinetic Parameters of Serum Fentanyl

| | SERUM FENTANYL | | | | | | | | | | | |
|---|---|---|---|---|---|---|---|---|---|---|---|---|
| | Treatment A | | | Treatment B | | | Treatment C | | | Treatment D | | |
| Pharmacokinetic Parameters | N | Arithmetic Mean | SD | N | Arithmetic Mean | SD | N | Arithmetic Mean | SD | N | Arithmetic Mean | SD |
| T½(hr) | 24 | 6.48 | 3.69 | 26 | 12.0 | 8.18 | 27 | 12.8 | 4.08 | 27 | 11.4 | 4.34 |
| Kel (1/hr) | 24 | 0.143 | 0.0802 | 26 | 0.0746 | 0.0377 | 27 | 0.0592 | 0.0167 | 27 | 0.0679 | 0.0216 |
| AUCR | 24 | 0.843 | 0.0604 | 26 | 0.875 | 0.0929 | 27 | 0.893 | 0.0589 | 27 | 0.909 | 0.0602 |
| $C_{max}$/dose (pg/mL/mcg) | 25 | 3.09 | 1.18 | 26 | 3.09 | 1.24 | 27 | 2.81 | 1.20 | 27 | 2.48 | 1.02 |
| AUC(0-t) (pg * hr/mL/mcg) | 25 | 14.4 | 5.54 | 26 | 17.0 | 6.69 | 27 | 16.4 | 5.02 | 27 | 15.6 | 4.84 |
| AUC(0-inf) (pg * hr/mL/mcg) | 24 | 17.7 | 6.52 | 26 | 19.4 | 7.30 | 27 | 18.5 | 5.81 | 27 | 17.3 | 5.80 |
| ln($C_{max}$/dose) | 25 | 1.06 | 0.383 | 26 | 1.05 | 0.426 | 27 | 0.945 | 0.439 | 27 | 0.836 | 0.386 |
| ln[AUC(0-t)/dose] | 25 | 2.59 | 0.424 | 26 | 2.75 | 0.441 | 27 | 2.75 | 0.324 | 27 | 2.69 | 0.356 |
| ln[AUC(0-int)/dose] | 24 | 2.81 | 0.369 | 26 | 2.89 | 0.413 | 27 | 2.87 | 0.329 | 27 | 2.79 | 0.372 |

*Median and min-max are reported for Tmax.
Treatment A = 1 × 200 mcg OraVescent Fentanyl Citrate Tablet
Treatment B = 1 × 500 mcg OraVescent Fentanyl Citrate Tablet
Treatment C = 1 × 810 mcg OraVescent Fentanyl Citrate Tablet
Treatment D = 1 × 1080 mcg OraVescent Fentanyl Citrate Tablet The slopes of ln [AUC(0-t)] versus ln(dose) and ln [AUC (0-inf)I versus ln(dose), at 1.0574 and 0.9983, respectively, 1, and the 90% CI for each parameter was completely contained within the critical range required for dose proportionality from 200 μg to 1080 μg. The slope of ln(Cmax) versus ln(dose), 0.8746, was less than 1 and the 90% CI (0.8145-0.9347) was not completely contained within the critical range required for the conclusion of dose proportionality. The maximal dose ratio such that the 90% CI for $\beta_1$ lay entirely within the critical range was 3.33. The maximal dose ratio such that the 90% CI for $\beta_1$ fell entirely outside the critical range was 30.48. The results of the ANOVA of dose-normalized Cmax for Treatments A, B, and C indicate that there was no statistically significant difference in dose-normalized Cmax in the dose range of 200 μg to 810 μg (p=0.13).

The primary objective of this study was to evaluate the extent to which dose proportionality exists for fentanyl AUC and Cmax following fentanyl doses of 200 μg (Treatment A), 500 μg (Treatment B), 810 μg (Treatment C), and 1080 μg (Treatment D) as OraVescent® Fentanyl Citrate tablets. In addition, this study was conducted to confirm previous observations relating to Cmax following the administration of 810 μg and 1080 μg doses of OraVescent® Fentanyl Citrate tablets. This study was a single-dose, randomized, open-label, 4-period crossover design.

Of the 28 subjects enrolled, 25 subjects completed Treatment A, 26 subjects completed Treatment B, and 27 subjects completed Treatments C and D. Statistical analysis was performed on the pharmacokinetic data for all subjects.

The slopes of ln [AUC(0-t)] versus ln(dose) and ln [AUC (0-inf)] versus ln(dose), at 1.0574 and 0.9983, respectively, were close to 1, and the 90% CI for each parameter was completely contained within the critical range required for dose proportionality. These results indicate that fentanyl AUC increased proportionally with each increasing dose level of OraVescent® Fentanyl Citrate tablets between the study doses of 200 μg to 1080 μg.

The slope of ln(Cmax) versus ln(dose), 0.8746, was less than 1, indicating that fentanyl Cmax increased less than proportionally to dose. The 90% CI (0.8145-0.9347) was not entirely contained within the critical range. The less than proportional increase was observed at the highest dose (1080 μg) and, to a lesser extent, at the second to highest dose (810 μg). Cmax increased proportionally from 200 μg to 500 μg. The value for $\rho_1$ (maximal dose ratio such that the 90% CI for $\beta_1$ lay entirely within the critical range) was 3.33, whereas the ratio of 810 μg:200 μg is 4.05. This indicates that the formulation is close to meeting the criteria for proportionality from the range of 200 μg to 810 μg according to this method. A secondary analysis using ANOVA to compare dose-normalized Cmax from the 200 μg, 500 μg, and 810 μg doses indicated no statistically significant difference (p=0.13) between these dose levels. The LS means for ln(Cmax/dose) were 1.06 (200 μg), 1.06 (500 μg), and 0.94 (810 μg), showing no difference between the 200 and 500 μg doses and a minimal (10%) difference in the 810 μg dose compared to the lower doses. The lack of significant result from the ANOVA in conjunction with the small magnitude in the difference between the 810 μg dose and the 2 lower doses indicates that there is not a clinically important deviation in dose proportionality in Cmax from 200 μg to 810 μg.

The mean dwell time for the 200 μg, 500 μg, 810 μg, and 1080 μg OraVescent® Fentanyl Citrate tablets were similar, at 14 minutes, 14 minutes, 17 minutes, and 15 minutes, respectively.

There were 2 subjects who reported minor irritation to the oral mucosa and 1 subject who experienced redness following the OraVescent® Fentanyl Citrate tablet.

Fentanyl AUC increased proportionally with increasing dose in the range of 200 μg to 1080 μg. Fentanyl Cmax increased less than proportionally to dose at the two highest dose levels. Mean ln(Cmax/dose) for the 810 μg dose was 10 to 11% lower than the 200 μg and 500 μg doses. Mean ln(Cmax/dose) for the 1080 μg dose was 20 to 21% lower than the 200 μg and 500 μg. There was not a clinically important deviation in dose proportionality in Cmax from 200 μg to 810 μg. The mean dwell time for the 200 μg, 500 μg, 810 μg, and 1080 μg OraVescent® Fentanyl Citrate tablets were similar, at 14 minutes, 14 minutes, 17 minutes, and 15 minutes, respectively.

There were no serious or unexpected adverse events during the study. Each formulation was well tolerated by the oral mucosa.

REFERENCES

8. Smith B P, et al. Confidence Interval Criteria for Assessment of Dose Proportionality. Pharmaceutical Research 17: 1278-1283, 2000.
9. SAS Institute, Inc., SAS®/STAT User's guide, Ver. 6. 4th ed. Vol. 1. Cary, N.C.: SAS Institute; 1989.
10. SAS Institute, Inc., SAS®/STAT Users guide, Ver. 6, 4th ed. Vol. 2. Cary, N.C.: SAS Institute; 1989.
11. SAS Institute, Inc., SAS® Procedures guide, Ver. 6, 3rd ed. Cary, N.C.: SAS Institute; 1990.
12. Summary Basis of Approval NDA 20-747 (Actiq®). Approval date Nov. 4, 1998, Clinical Pharmacology and Biopharmaceutics Review pp 6.

Any formulation which contains sufficient effervescent material and pH adjusting substance, preferably with a suitable disintegrant which is capable of providing a dosage form useful in buccal, gingival, or sublingual administration of fentanyl at dose levels which are contemplated herein and provides the dose reductions and/or $C_{max}$ to dose relationships described herein may be used. Most preferably, for dosage forms containing about 100 to about 1,000 micrograms of fentanyl (calculated as free base) or a proportionate amount of a salt, any effervescent couple and/or pH adjusting substance which can be provided in an amount that produces a dosage form having a $T_{max}$ of 1.5 hours or less and/or provides a $C_{max}$ to dose of between about 2.0 and about 4.0 picograms/mL/micrograms, more preferably between about 2.5 and about 3.5, and even more preferably between about 2.7 and about 3.5 picograms/mL/micrograms may be used.

Similarly, any amount of effervescent couple and pH adjusting substance which provides a dosage form having comparable $C_{max}$ when compared to an ACTIQ formulation having at least about 80% more fentanyl is contemplated. That is, it has a $C_{max}$ of at least 75% to 125% of the $C_{max}$ of such an ACTIQ formulation, more preferably between about 80% and about 125% and most preferably between about 85% and about 115% of an ACTIQ formulation, despite having at least 45% less fentanyl (calculated as the freebase). Note that there is no 2 milligram ACTIQ presently on the market. But comparisons of the 1,000-1,080 microgram dosage form of the invention is intended to be compared to an ACTIQ style product having 2 milligrams of fentanyl, calculated as a free base. In a particularly preferred embodiment, these formulations will not include a significant amount of any disintegrant or excipient or combination of excipients which will interfere with such performance characteristics. Spray dried mannitol is a preferred filler. Another preferred excipient is a disintegrant which is a starch glycolate, and in particular, sodium starch glycolate. The former is typically characterized by those skilled in the art as a filler and the latter a disintegrant. However, such characterizations are not controlling.

Formulations in the '604 patent which included lactose monohydrate in an amount of greater than 20% and/or microcrystalline cellulose in an amount of at least about 20% and cross-linked PVP in an amount of 5% or more, including the formulation in Example 1, are believed to be unable to provide formulations having the desirable properties of the invention despite the presence of a pH adjusting substance and an effervescent couple.

A preferred effervescent, orally disintegrable, dosage form in accordance with the present invention is one that includes, based on the weight of the free base material, between about 100 and 1000 micrograms of fentanyl, or a proportionate weight of one of its pharmaceutically acceptable salts. Most preferred amongst such salts is fentanyl citrate. More preferably, the dosage forms will include between about 100 and about 880 micrograms of fentanyl. Most preferably, the amount will range from between about 100 to about 800 micrograms. In addition, these numbers are meant to include normal processing variabilities such as content uniformity, etc. Particularly preferred doses are about 100 micrograms, about 200 micrograms, about 300 micrograms, about 400 micrograms, about 600 micrograms and about 800 micrograms, and about 1000 micrograms, respectively.

It is preferred that the mean particle size, as determined by a laser diffraction technique, of fentanyl used in the present formulation range from about 0.2 to about 150 microns, more preferably from about 0.5 to about 100 and most preferably from about 1 to about 20 microns.

As an effervescent agent or effervescent couple, any known combination may be used. These include those described in U.S. Pat. No. 5,178,878 and U.S. Pat. No. 5,503,846, the texts of which are hereby incorporated by reference to the extent they discuss various effervescent couples and constructions of same. Effervescent couples generally are water- or saliva-activated materials usually kept in a anhydrous state with little or no absorbed moisture or in a stable hydrated form. Typically these involve at least one acid source and at least one source of a reactive base, usually a carbonate or bicarbonate. Each of the components of the effervescent couple may be any which are safe for human consumption.

The acids generally include food acids, acid anhydrides and acid salts. Food acids include citric acid, tartaric acid, malic acid, fumeric acid, adipic acid, ascorbic acid and succinic acid. Acid anhydrides or salts of these acids may be used. Salts in this context may include any known salt but in particular, sodium, dihydrogen phosphate, disodium dihydrogen phosphate, acid citrate salts and sodium acid sulfate. Bases useful in accordance with the invention typically include sodium bicarbonate, potassium bicarbonate and the like. Sodium carbonate, potassium carbonate, magnesium carbonate and the like may also be used to the extent they are used as part of an effervescent couple. However, they are more preferably used as a pH adjusting substance. Preferably, stoichiometric equivalent amounts of acid and base are used. It is possible, however, that some excess of acid, acid anhydrate, or acid salt or base be used. However, care should be exercised when so formulating a formulation particularly in view of the overall pH adjusting effect of such components, if any. An excess could affect absorption.

The amount of effervescent material useful in accordance with the present invention is an effective amount and is determined based on properties other than those which would be necessary to achieve disintegration of the tablet in the mouth. Instead, effervescence is used as a basis for enhancing transmission of the fentanyl across mucosal membranes via buccal, gingival or sublingual administration in the oral cavity. Accordingly, the amount of effervescent couple should range from between about 5 to about 85 percent, more preferably between about 15 to 60 percent, even more preferably between about 30 and 45 percent and most preferably between about 35 to about 40 percent, based on the weight of the total formulation. Of course, the relative proportion of acid base will depend upon the specific ingredients (for example, whether the acid monoprotic, diprotic or triprotic) relative molecular weights, etc. However, preferably, a stoichiometric amount of each is provided although, of course, excesses are acceptable.

Preferably, formulations in accordance with the present invention include at least one pH adjusting substance. In this manner, a drug that is susceptible to changes in ionization state can be administered by effecting the proper conditions for its dissolution as well as transmission across one or more of the membranes or tissues within the oral cavity, for example, the oral mucosa. If the ideal conditions for transmission of a particular drug are basic, the addition of a sufficient excess of suitably strong acid as part of the manufacture of an effervescent couple or as a pH adjusting substance may not be indicated. The selection of another pH adjusting substance such as, for example, anhydrous sodium carbonate which operates separate and apart from the effervescent agents would be preferred.

pH adjusting substances in accordance with the present invention can be used to provide further permeation enhancement. The selection of the appropriate pH adjusting substance will depend on the drug to be administered and, in particular, to the pH at which it is ionized or unionized, and whether the ionized or unionized form facilitates transmission across the oral mucosa. With regard to fentanyl and its salts, a basic substance is preferred for the delivery of fentanyl. pH adjusting substances in accordance with the present invention can include, without limitation, any substance capable of adjusting the localized pH to promote transport across the membranes in the oral cavity in amounts which will result in a pH's generally ranging from between about 3 to 10 and more preferably between about 4 to about 9. The pH is the "localized pH" at the microenvironment in the mouth of a patient at the surface contact area of the oral mucosa and the dosage form or any portion thereof (such as when it disintegrates). For purposes of this invention, the localized pH can be determined as follows: to characterize the dynamic pH changes displayed by the tablets in question, an in vitro pH measurement was used. The method consists of using 0.5-10 mL of phosphate buffered saline in an appropriately sized test tube or similar vessel. The amount of media is dependent on the tablet size and dosage. For example, when measuring the pH profile for fentanyl tablets, a volume of 1 mL was used for tablets which weighed 100 mg. Immediately upon tablet contact with the media, the pH profile of the solution is monitored as a function of time, using a micro-combination pH electrode. Preferably, the materials which can be used as pH adjusting substances in accordance with the present invention include carbonates such as sodium, potassium or calcium carbonate or a phosphate such as calcium or sodium phosphate. Most preferred is sodium carbonate. The amount of pH adjusting substance useful in accordance with the present invention can vary with the type of pH adjusting substance used, the amount of any excess acid or base from the effervescent couple, the nature of the remaining ingredients and, of course, the drug which, in this case, is fentanyl.

Most preferably the amount of pH adjusting substance will range from between about 0.5 to about 25 percent, more preferably between about 2 to about 20 percent, even more preferably between about 5 to about 15 percent and most preferably between about 7 to about 12 percent by weight based on the weight of the total formulation. The most preferred pH adjusting substance is a carbonate, bicarbonate, or phosphate. Also preferred are those pH adjusting substances which, when provided in a suitable amount, can provide a change in the localized pH of at least about 0.5 pH units, more preferably about 1.0 pH units and even more preferably about 2.0 pH units when compared to an otherwise identical formulation without the pH adjusting substance.

Any filler or any amount of a filler may be used as long as the resulting dosage forms achieve the results described herein. Most preferred amongst the fillers are sugar and sugar alcohols and these may include non-direct compression and direct compression fillers. Non-direct compression fillers generally, at least when formulated, have flow and/or compression characteristics which make them impractical for use in high speed tableting process without augmentation or adjustment. For example, a formulation may not flow sufficiently well and therefore, a glidant such as, for example, silicon dioxide may need to be added.

Direct compression fillers, by contrast, do not require similar allowances. They generally have compressibility and flowability characteristics which allow them to be used directly. It is noted that, depending upon the method by which formulations are made, non-direct compression fillers may be imparted with the properties of direct compression fillers. The reverse is also true. As a general matter, non-direct compression fillers tend to have a relatively smaller particle size when compared to direct compression fillers. However, certain fillers such as spray dried mannitol have relatively smaller particle sizes and yet are often directly compressible, depending upon how they are further processed. There are also relatively large nondirect compression fillers as well.

Fillers that are preferred in accordance with the present invention include mannitol, lactose, sorbitol, dextrose, sucrose, xylitol and glucose, to the extent their use can provide the results described herein. More preferably in accordance with the present invention, the filler is not lactose monohydrate used in an amount of 20% or more based on the weight of the formulation and even more preferably no lactose monohydrate is used. Most preferred in accordance with the present invention, spray dried mannitol is used. The amount of filler can range from 10 to about 80% and more preferably about 25 to about 80%, most preferably 35 to about 60% by weight of the formulation.

Disintegrants may also be used in accordance with the present invention so long as they permit or even facilitate the dose reductions and/or ratio of Cmax and dose as described herein. These may also include binders that have disintegrating properties. Disintegrants in accordance with the present invention can include microcrystalline cellulose, cross-linked polyvinyl pyrrolidone (PVP-XL), sodium starch glycolate, croscarmellose sodium, cross-linked hydroxypropyl cellulose and the like. Of course, the selection of the disintegrant depends upon whether or not, in a given system, the results described herein may be obtained. More preferably, the formulation will be free of more than about 20% microcrystalline cellulose and cross-linked polyvinyl pyrrolidone in an amount of about 5% or more, especially in a formulation that includes in additional 20% lactose monohydrate. Most preferred for use as a disintegrant is a starch glycolate and in particular sodium starch glycolate. Indeed, it has been found that the use of sodium starch glycolate in the formulations of the present invention can provide significant improvement in the degree of dose reduction, while still providing a comparable Cmax, when compared to effervescent formulations which include pH adjusting substances and other disintegrants. A particularly useful sodium starch glycolate is GLYCOLYS® (standard grade) available from Roquette of Lestrem France. Indeed, it is even more preferred that the formulation include neither microcrystalline cellulose nor cross-linked PVP.

The amount of disintegrant will vary with known factors such as, the size of the dosage form, the nature and amounts of the other ingredients used, etc. However, in general the amount should range from between about 0.25 to about 20% by weight of the final formulation, more preferably between about 0.5 to about 15% w/w, even more preferably 0.5 to about 10% w/w and even more preferably between about one and about eight percent by weight. This is again based on the weight of the finished formulation.

Also generally useful in accordance with the present invention is a tableting or ejection lubricant. The most common known lubricant is magnesium stearate and the use of magnesium stearate is preferred. Generally, the conventional wisdom behind tableting lubricants is that less is more. It is preferred in most circumstances that less than about one percent of a tableting lubricant be used. Typically, the amount should be half a percent or less. However, the amount of magnesium stearate used can be greater than 1.0%. Indeed, it is preferably greater than about 1.5% and most preferably about 1.5% and about 3%. Most preferred is the use of about 2% magnesium stearate. Other conventional tableting lubricants such as, for example, stearic acid, calcium stearate and the like may also be used in place of some or all of the magnesium stearate.

Effervescent tablets in accordance with the present invention can be relatively soft or robust. They can, for example, be manufactured in accordance with the methods described in U.S. Pat. No. 5,178,878 and will have a hardness of generally less than about 15 Newtons. Unlike the formulations described in the '878 patent, the active ingredient here will not necessarily be coated with a protective material. Indeed, preferentially, the fentanyl active will not be coated. When tablets as soft and pliable/friable as these are produced, they may be advantageously packaged in a blister package such as found in U.S. Pat. No. 6,155,423. They may also be robust with a hardness of greater than about 15 newtons, manufactured in accordance with the procedures set forth in U.S. Pat. No. 6,024,981.

In a preferred embodiment, the fentanyl dosage forms of the invention are provided in a blister package which is child resistant. See for example U.S. Pat. No. 6,155,423 to Katzner et al., issued Dec. 5, 2000 and assigned to CIMA LABS INC., the text of which is hereby incorporated by reference. Most preferably, the package meets the standards set forth in 16 U.S.C. §1700.15 and 0.20 (2003). Packages also preferred include those commonly referred to in the industry as so-called "F1" and "F2" packages. "F1" packages are most preferred.

Tablets in accordance with the present invention may be designed slightly differently for buccal, gingival, or sublingual administration. In each instance, however, the in mouth disintegration time/dissolution (dwell time) achieved by the formulations is preferably less than about 30 minutes and most preferably, about 20 minutes or less. It is usually more than five minutes, most often 10 minutes or more. This is a subjective determination based on the response of the patient.

In accordance with a particularly preferred embodiment of the present invention, there is provided an effervescent orally disintegrable tablet designed for buccal, sublingual or gingival administration of fentanyl, or pharmaceutically acceptable salt thereof, comprising between 100 and 1000 micrograms of fentanyl (by weight based on the weight of the free base), an effective amount of an effervescent couple and an effective amount of a pH adjusting substance. The formulation may further include one or more excipients.

In a particularly preferred aspect of this embodiment of the present invention, the formulations described above do not include an amount of lactose monohydrate and/or crosslinked PVP which render it incapable of obtaining a dose reduction relative to ACTIQ® of at least about 45% fentanyl by weight. In particular, it is preferred that no more than about 10% by weight of the formulation be lactose monohydrate or microcrystalline cellulose and no more than about 4% crosslinked PVP. More preferably, the formulation is free from all but incidental amounts of these excipients. Most preferred in accordance with the present invention are the use of sodium starch glycolate as a disintegrant and mannitol as a filler. Most preferred filler includes spray dried mannitol.

The formulations in accordance with the present invention can include other conventional excipients in generally known amounts to the extent they do not detract from the advantages described herein. These can include without limitation binders, sweeteners, coloring components, flavors, glidants, lubricants, preservatives, disintegrants, and the like.

Tablets, a preferred dosage form in accordance with the present invention, can be made by any known tableting technique. However, preferably, the materials used are dry blended and directly compressed. While the tablets may result from granulation, this is not preferred. Of course, particular excipients and materials used in formulations in accordance with the present invention may be wet or dry granulated. For example, granulated mannitol could be used as a filler. It may also be desirable to granulate or pre-mix some portion of the formulation prior to final blending and compression. The materials in question are preselected to provide the right dose and content uniformity and the dose reduction, Cmax/dose ratio and/or dose linearity described herein. Thus, an appropriate amount of an effervescent couple, a suitable and appropriate pH adjusting substance and an appropriate disintegrant are selected, provided in predetermined amounts and formulated to dosage forms, preferably tablets.

The preferred pH adjusting substances are carbonates, bicarbonates, or phosphates, the preferred disintegrant is a starch glycolate. The amounts used of each are described elsewhere herein. However, preferably, the disintegrant is selected and provided in an amount which can provide a further dose reduction in the amount of fentanyl used when compared to an otherwise identical formulation containing an effervescent couple and a pH adjusting substance without the disintegrant. The pH adjusting substance preferably is selected and provided in an amount sufficient which is capable of providing a change in localized pH of at least 0.5 pH units, more preferably 1.0 pH unit and most preferably about 2.0 pH units or more. While tablets may be compressed to any hardness and/or friability, same must be accomplished without adversely affecting dwell times and drug release and transmission across the oral mucosa. Where possible, it is desirable to provide fentanyl dosage forms as compressed tablets having a hardness of between about 5 and about 100 Newtons, more preferably between about 10 and about 50 Newtons.

The dosage forms in accordance with the present invention may be used to treat any type of pain and in particular pain for which opiates are commonly prescribed. As with all opiates, fentanyl products and particularly those of the present invention should always be taken in consultation with a doctor and under a physician's strict care and supervision. The general directions for the use of the ACTIQ product as found in the previously mentioned label found in the Physician's Desk Reference and the warnings and contraindications therein are broadly applicable to the use of dosage forms in accordance with the present invention. This includes generally titrating patients with lower doses before dose escalation.

The dosage forms in accordance with the present invention are administered by being placed in the mouth of a patient, preferably under the tongue or in between the cheek and gum, where they remain until their dissolution/disintegration is substantially complete and they cease to be recognizable as a dosage form. Preferably, swallowing is minimized to assist in facilitating the maximum transfer of the fentanyl across the adjacent oral mucosa.

Additional doses are taken as needed. As previously noted, a single dose such as, for example, 800 micrograms of fentanyl, can be taken in a single dosage form in accordance with the present invention or can be taken in a plurality of dosage forms such as, for example, two dosage forms of the present invention each containing 400 micrograms of fentanyl or four dosage forms in accordance with the present invention each containing approximately 200 micrograms of fentanyl. Preferably such multiple dosage form dosing will involve all of the dosage forms being administered within an hour, more preferably roughly contemporaneously if not simultaneously.

In particular, one method of making a tablet in accordance with the present invention useful for buccal, gingeval, or sublingual administration comprises providing fentanyl or a salt thereof in an amount of between about 100 and about 1000 micrograms per dose (measured as fentanyl base), or an equivalent amount of salt thereof. Also provided are an effervescent couple in an amount of 5 to about 85% by weight of the dosage form, a pH adjusting substance in an amount of between about 0.5 and about 25% by weight of the dosage form and a disintegrant, preferably a starch glycolate, provided in an amount between about 0.25 to about 20% by weight of the dosage form. These are blended and compressed into tablets. In a preferred embodiment, the filler is used as well. In a particular preferred embodiment, a portion of the filler may be preblended with the fentanyl or another excipient such as, for example, a coloring agent.

In addition, one of the excipients often used in accordance with the present invention is a lubricant such as magnesium stearate. Generally this is added toward the end of the blending period. Blending is often interrupted and then magnesium steriate is added before blending resumes for few additional minutes.

In a preferred embodiment, a blister package containing a dosage from and in accordance with the present invention should be opened immediately prior to the product's use. The patient should place the dosage form in his or her mouth, preferably between the cheek and the upper or lower gum. The dosage form should not be sucked or chewed. Fentanyl, as with many opiates, is preferably titrated with the initial dose being a relatively low dose. The initial dose for dosage forms for fentanyl formulations in accordance with the present invention, especially those used to treat episodes of breakthrough cancer pain, should be 100 micrograms. The patient should be provided with a limited initial titration supply of 100 microgram dosage forms, thus limiting the number of units in the home during titration. Thereafter, doses may be escalated under a doctor's care.

EXAMPLES

Method of Manufacture

In each case for examples 1-7 and 9-11, materials were screened prior to use, charged into a V-blender, or can be blended in any other appropriate low shear blender, and blended for an appropriate time. After discharge from the blender, the materials were compressed on a standard rotary tablet press to a target hardness of 13 Newtons and a target weight of 100 or 200 mg as described in each example.

Example 1

Form A

| OraVescent ® Fentanyl, 1080 mcg, 5/16" Tablet, Red | |
|---|---|
| COMPONENT NAME | QUANTITY (mg/tab) |
| Fentanyl Citrate, USP | 1.688 |
| Mannitol, USP* | 95.312 |
| Sodium Bicarbonate, USP/EP/JP | 42.000 |
| Citric Acid, USP/EP/JP | 30.000 |
| Sodium Carbonate, USP/NF | 20.000 |
| Sodium Starch Glycolate, NF/EP | 6.000 |
| Magnesium Stearate, NF/EP/JP | 4.000 |
| Red Ferric Oxide, NF | 1.000 |
| TOTAL | 200.000 |

*spray dried (Mannogen EZ by SPI Pharma)

Example 2

Form C

| OraVescent ® Fentanyl, 1300 mcg, 5/16" Tablet, Red | |
|---|---|
| COMPONENT NAME | QUANTITY (mg/tab) |
| Fentanyl Citrate, USP | 2.042 |
| Mannitol, USP* | 94.958 |
| Sodium Bicarbonate, USP/EP/JP | 42.000 |
| Citric Acid, USP/EP/JP | 30.000 |
| Sodium Carbonate, USP/NF | 20.000 |
| Sodium Starch Glycolate, NF/EP | 6.000 |
| Magnesium Stearate, NF/EP/JP | 4.000 |
| Red Ferric Oxide, NF | 1.000 |
| TOTAL | 200.000 |

*spray dried

Example 3

Form D

| OraVescent ® Fentanyl, 810 mcg, 5/16" Tablet, Yellow | |
|---|---|
| COMPONENT NAME | QUANTITY (mg/tab) |
| Fentanyl Citrate, USP | 1.266 |
| Mannitol, USP* | 95.734 |
| Sodium Bicarbonate, USP/EP/JP | 42.000 |
| Citric Acid, USP/EP/JP | 30.000 |
| Sodium Carbonate, USP/NF | 20.000 |
| Sodium Starch Glycolate, NF/EP | 6.000 |
| Magnesium Stearate, NF/EP/JP | 4.000 |
| Yellow Ferric Oxide, NF | 1.000 |
| TOTAL | 200.000 |

*spray dried

Example 4

Form E

| OraVescent ® Fentanyl, 270 mcg, 5/16" Tablet, White | |
|---|---|
| COMPONENT NAME | QUANTITY (mg/tab) |
| Fentanyl Citrate, USP | 0.422 |
| Mannitol, USP* | 97.578 |
| Sodium Bicarbonate, USP/EP/JP | 42.000 |
| Citric Acid, USP/EP/JP | 30.000 |
| Sodium Carbonate, USP/NF | 20.000 |
| Sodium Starch Glycolate, NF/EP | 6.000 |
| Magnesium Stearate, NF/EP/JP | 4.000 |
| TOTAL | 200.000 |

*spray dried

Example 5

| OraVescent ® Fentanyl, 500 mcg, 5/16" Tablet, Orange | |
|---|---|
| COMPONENT NAME | QUANTITY (mg/tab) |
| Fentanyl Citrate, USP | 0.786 |
| Mannitol, USP* | 96.214 |
| Sodium Bicarbonate, USP/EP/JP | 42.000 |
| Citric Acid, USP/EP/JP | 30.000 |
| Sodium Carbonate, NF | 20.000 |
| Sodium Starch Glycolate, NF/EP | 6.000 |
| Magnesium Stearate, NF/EP/JP | 4.000 |
| Yellow Ferric Oxide, NF | 0.600 |
| Red Ferric Oxide, NF | 0.400 |
| TOTAL | 200.000 |

*spray dried

Example 6

| OraVescent ® Fentanyl, 200 mcg, 5/16" Tablet, White | |
|---|---|
| COMPONENT NAME | QUANTITY (mg/tab) |
| Fentanyl Citrate, USP | 0.315 |
| Mannitol, USP* | 97.685 |
| Sodium Bicarbonate, USP/EP/JP | 42.000 |
| Citric Acid, USP/EP/JP | 30.000 |
| Sodium Carbonate, NF | 20.000 |
| Sodium Starch Glycolate, NF/EP | 6.000 |
| Magnesium Stearate, NF/EP/JP | 4.000 |
| TOTAL | 200.000 |

*spray dried

Example 7

| OraVescent ® Fentanyl, 100 mcg, ¼" Tablet, White | |
|---|---|
| COMPONENT NAME | QUANTITY (mg/tab) |
| Fentanyl Citrate, USP | 0.157 |
| Mannitol, USP* | 48.843 |
| Sodium Bicarbonate, USP/EP/JP | 21.000 |
| Citric Acid, USP/EP/JP | 15.000 |
| Sodium Carbonate, NF | 10.000 |
| Sodium Starch Glycolate, NF/EP | 3.000 |
| Magnesium Stearate, NF/EP/JP | 2.000 |
| TOTAL | 100.000 |

*spray dried

Example 8

The materials may be screened prior to use, charged into a V-blender or other appropiate low shear blender, and blended for an appropriate time. After discharge from the blender, the materials may be compressed on a standard rotary tablet press to a target hardness of 13 Newtons and a target weight of 200 mg/tablet.

| OraVescent ® Fentanyl, 300 mcg, 5/16" Tablet, Light Yellow | |
|---|---|
| COMPONENT NAME | QUANTITY (mg/tab) |
| Fentanyl Citrate, USP | 0.472 |
| Mannitol, USP* | 97.328 |
| Sodium Bicarbonate, USP/EP/JP | 42.000 |
| Citric Acid, USP/EP/JP | 30.000 |
| Sodium Carbonate, NF | 20.000 |
| Sodium Starch Glycolate, NF/EP | 6.000 |
| Magnesium Stearate, NF/EP/JP | 4.000 |
| Yellow Ferric Oxide, NF | 0.200 |
| TOTAL | 200.000 |

*spray dried

Example 9

| OraVescent ® Fentanyl, 400 mcg, 5/16" Tablet, Pink | |
|---|---|
| COMPONENT NAME | QUANTITY (mg/tab) |
| Fentanyl Citrate, USP | 0.629 |
| Mannitol, USP* | 97.171 |
| Sodium Bicarbonate, USP/EP/JP | 42.000 |
| Citric Acid, USP/EP/JP | 30.000 |
| Sodium Carbonate, NF | 20.000 |
| Sodium Starch Glycolate, NF/EP | 6.000 |
| Magnesium Stearate, NF/EP/JP | 4.000 |
| Red Ferric Oxide, NF | 0.200 |
| TOTAL | 200.000 |

*spray dried

Example 10

| OraVescent ® Fentanyl, 600 mcg, 5/16" Tablet, Orange | |
|---|---|
| COMPONENT NAME | QUANTITY (mg/tab) |
| Fentanyl Citrate, USP | 0.943 |
| Mannitol, USP* | 96.057 |
| Sodium Bicarbonate, USP/EP/JP | 42.000 |
| Citric Acid, USP/EP/JP | 30.000 |
| Sodium Carbonate, NF | 20.000 |
| Sodium Starch Glycolate, NF/EP | 6.000 |
| Magnesium Stearate, NF/EP/JP | 4.000 |
| Yellow Ferric Oxide, NF | 0.600 |
| Red Ferric Oxide, NF | 0.400 |
| TOTAL | 200.000 |

*spray dried

Example 11

| OraVescent ® Fentanyl, 800 mcg, 5/16" Tablet, Yellow | |
|---|---|
| COMPONENT NAME | QUANTITY (mg/tab) |
| Fentanyl Citrate, USP | 1.257 |
| Mannitol, USP* | 95.743 |
| Sodium Bicarbonate, USP/EP/JP | 42.000 |
| Citric Acid, USP/EP/JP | 30.000 |
| Sodium Carbonate, NF | 20.000 |
| Sodium Starch Glycolate, NF/EP | 6.000 |
| Magnesium Stearate, NF/EP/JP | 4.000 |
| Yellow Ferric Oxide, NF | 1.000 |
| TOTAL | 200.000 |

*spray dried

Example 12

The materials may be screened prior to use, charged into a V-blender or other appropirate low shear blender, and blended for an appropriate time. After discharge from the blender, the materials may be compressed on a standard rotary tablet press to a target hardness of 13 Newtons and a target weight of 200 mg/tablet.

| OraVescent ® Fentanyl, 1000 mcg, 5/16" Tablet, Red | |
|---|---|
| COMPONENT NAME | QUANTITY (mg/tab) |
| Fentanyl Citrate, USP | 1.571 |
| Mannitol, USP* | 95.429 |
| Sodium Bicarbonate, USP/EP/JP | 42.000 |
| Citric Acid, USP/EP/JP | 30.000 |
| Sodium Carbonate, NF | 20.000 |
| Sodium Starch Glycolate, NF/EP | 6.000 |
| Magnesium Stearate, NF/EP/JP | 4.000 |
| Red Ferric Oxide, NF | 1.000 |
| TOTAL | 200.000 |

*spray dried

Example 13

The following materials are weighed and screened.

| # | Description | Qty./Tablet (% w/w) | Qty./Batch (kg) |
|---|---|---|---|
| 1 | Fentanyl Citrate | 0.6285 | 502.8 g* |
| 2a. | Mannitol EZ | 23.875 | 19.1 |
| 2b. | Mannitol EZ | 24.014 | 19.2 |
| 3. | Sodium Bicarbonate, No. 1 | 21.0000 | 16.8 |
| 4. | Citric Acid, Anhydrous, Fine Granular | 15.0000 | 12.0 |
| 5. | Sodium Carbonate, Anhydrous | 10.0000 | 8.000 |
| 6. | Sodium Starch Glycolate | 3.0000 | 2.400 |
| 7. | Yellow 10 Iron Oxide | 0.5000 | 0.400 |
| 8. | Magnesium Stearate, Non-Bovine | 2.0000 | 1.600 |
| | Total | 100.0000 | 80.0 |

Transfer Mannitol EZ (2a.) and Yellow 10 Iron Oxide to V-blender and blend for 30 minutes. Discharge and mill preblend. Add the total quantity of preblend, fentanyl citrate, sodium bicarbonate, citric acid, sodium carbonate and sodium starch glycolate to V-blender and blend for 30 minutes. Charge Mannitol (2b) into V-blender and blend for 13 minutes. Charge magnesium stearate into V-blender and blend for 5 minutes. Compress tablets from this final blend. These tablets are ¼" round, flat faced, white with a beveled edge. They are compressed to an average hardness of 13 Newtons on a 36 station Fette tablet press fully tooled.

We claim:

1. A dosage form comprising:
   about 1000 micrograms of fentanyl, calculated as fentanyl free base or an equivalent amount of a salt thereof,
   an effervescent couple in an amount of about 15% to no more than about 60% by weight of the dosage form,
   a pH adjusting substance in an amount of about 0.5 to about 25% by weight of the dosage form, wherein said pH adjusting substance is not a component of said effervescent couple,
   mannitol in an amount of between about 10 and about 80% by weight of the dosage form;
   a starch glycolate in an amount of about 0.25 to about 20% by weight of the dosage form,
   said dosage form being suitable for delivery of said fentanyl across the oral mucosa of a patient by buccal, gingival or sublingual administration.

2. The dosage form of claim 1 wherein said pH adjusting substance is selected and provided in an amount capable of providing a change in localized pH of at least 0.5 pH units.

3. The dosage form of claim 2 wherein said pH adjusting substance is a carbonate, phosphate or bicarbonate.

4. The dosage form of claim 1 being a compressed tablet.

5. A dosage form comprising:
   about 1000 micrograms of fentanyl, calculated as fentanyl free base or an equivalent amount of a salt thereof,
   an effervescent couple in an amount of about 15% to no more than about 60% by weight of the dosage form,
   a pH adjusting substance said adjusting substance selected and provided in an amount capable of providing a change in localized pH of at least 0.5 pH units, wherein said pH adjusting substance is not a component of said effervescent couple, mannitol in an amount of between about 10 and about 80% by weight of the dosage form;
and
a starch glycolate,
said dosage form adapted for delivery of said fentanyl across the oral mucosa of a patient by buccal, gingival or sublingual administration.

6. The dosage form of claim 5 wherein said pH adjusting substance is present in an amount of about 0.5 to about 25% by weight of said dosage form, and said starch glycolate is present in an amount of about 0.25 to about 20% by weight of the dosage form.

7. The dosage form of claim 6 wherein said pH adjusting substance is present in an amount of about 2 to about 20% by weight of said dosage form, and said starch glycolate is present in an amount of about 0.5 to about 15% by weight of the dosage form.

8. A method of treating pain in a patient in need thereof comprising the steps of: placing a dosage form according to claim 5 into the mouth of a patient in contact with said patient's oral mucosa, and maintaining said dosage form in intimate contact with said oral mucosa for a time sufficient to deliver a therapeutically effective amount of said fentanyl across said oral mucosa.

9. The method of claim 8 wherein said dosage form is held in contact with said oral mucosa for a period of between about 10 and about 30 minutes.

10. The method of claim 9 wherein said dosage form is held in contact with said oral mucosa for a period of time sufficient to provide absorption of at least about 75% of said fentanyl dose into the blood stream of said patient.

11. The method of claim 8, wherein said pain is selected from the group consisting of back pain, breakthrough cancer pain, neuropathic pain, surgical pain and postoperative pain.

12. A method of making a dosage form according to claim 7 in the form of a tablet for buccal, gingival or sublingual administration of fentanyl comprising the steps of: providing said fentanyl or a salt thereof in an amount of between about 1000 micrograms per dose measured as fentanyl base, or an equivalent amount of a salt thereof, providing said effervescent couple in an amount of about 5 to about 85% by weight of the dosage form, said pH adjusting substance in an amount of about 0.5 to about 25% by weight of the dosage form, and said starch glycolate in an amount of about 0.25 to about 20% by weight of the dosage, blending said fentanyl, effervescent couple, pH adjusting substance and said starch glycolate, and compressing the resulting blend into at least one tablet.

13. The method of claim 12 further comprising the step of packaging said tablet in an F1 package.

14. The method of claim 12 further comprising the step of providing a filler in an amount of between about 10 and about 80% by weight of the dosage form and blending same with said fentanyl, effervescent couple, pH adjusting substance and said starch glycolate prior to compressing the resulting blend into at least one tablet.

* * * * *